US009782484B2

(12) United States Patent
Hirokawa et al.

(10) Patent No.: US 9,782,484 B2
(45) Date of Patent: Oct. 10, 2017

(54) METHOD FOR PRODUCING A COMPOSITE ORGANIC COMPOUND POWDER FOR MEDICAL USE

(71) Applicant: ACTIVUS PHARMA CO., LTD., Funabashi-shi, Chiba (JP)

(72) Inventors: Takashi Hirokawa, Chiba (JP); Takahiro Tada, Chiba (JP); Jun Nihira, Ibaraki (JP)

(73) Assignee: ACTIVUS PHARMA CO., LTD., Chiba (JP)

( * ) Notice: Subject to any disclaimer, the term of this patent is extended or adjusted under 35 U.S.C. 154(b) by 154 days.

(21) Appl. No.: 14/010,602

(22) Filed: Aug. 27, 2013

(65) Prior Publication Data

US 2014/0038931 A1   Feb. 6, 2014

Related U.S. Application Data

(62) Division of application No. 13/063,026, filed as application No. PCT/JP2009/004596 on Sep. 15, 2009, now abandoned.

(30) Foreign Application Priority Data

Sep. 19, 2008   (JP) .................................. 2008-241855

(51) Int. Cl.
| | |
|---|---|
| *A61K 47/34* | (2017.01) |
| *A61K 9/10* | (2006.01) |
| *A61K 9/14* | (2006.01) |
| *A61K 31/4174* | (2006.01) |
| *A61K 31/222* | (2006.01) |
| *A61K 31/573* | (2006.01) |
| *A61K 47/24* | (2006.01) |
| *A61K 47/26* | (2006.01) |
| *A61K 47/32* | (2006.01) |
| *A61K 31/41* | (2006.01) |
| *A61K 31/192* | (2006.01) |
| *A61K 31/405* | (2006.01) |

(52) U.S. Cl.
CPC ............... *A61K 47/34* (2013.01); *A61K 9/10* (2013.01); *A61K 9/146* (2013.01); *A61K 31/192* (2013.01); *A61K 31/222* (2013.01); *A61K 31/405* (2013.01); *A61K 31/41* (2013.01); *A61K 31/4174* (2013.01); *A61K 31/573* (2013.01); *A61K 47/24* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 4,343,789 A | * | 8/1982 | Kawata .................. | A61K 9/146 424/497 |
| 5,145,684 A | * | 9/1992 | Liversidge et al. .......... | 424/489 |
| 5,914,118 A | | 6/1999 | Yamamura et al. | |
| 8,105,691 B2 | * | 1/2012 | Takeuchi et al. ............. | 428/407 |
| 2002/0012704 A1 | | 1/2002 | Pace et al. | |
| 2003/0224058 A1 | * | 12/2003 | Ryde ....................... | A61K 9/145 424/489 |
| 2004/0260083 A1 | | 12/2004 | Shiromaru et al. | |
| 2006/0058531 A1 | * | 3/2006 | Hosaka ................. | C07D 235/26 548/305.4 |
| 2007/0178051 A1 | | 8/2007 | Pruitt et al. | |
| 2007/0256604 A1 | * | 11/2007 | Garcia Luna ........... | C04B 28/04 106/728 |
| 2008/0152720 A1 | | 6/2008 | Jenkins et al. | |
| 2009/0062240 A1 | * | 3/2009 | Edgar .................. | A61K 31/216 514/163 |
| 2010/0016597 A1 | | 1/2010 | Hirokawa et al. | |

FOREIGN PATENT DOCUMENTS

| | | |
|---|---|---|
| EP | 1849830 A1 | 10/2007 |
| JP | 03-066613 A | 3/1991 |
| JP | 03-131355 A | 6/1991 |
| JP | 04-295420 A | 10/1992 |
| JP | 06-228454 A | 8/1994 |
| JP | 11-100317 A | 4/1999 |
| JP | 2003-286105 A | 10/2003 |
| JP | 2003-342493 A | 12/2003 |
| JP | 2005-008806 A | 1/2005 |
| JP | 2006-255519 A | 9/2006 |
| JP | 2007-023051 A | 2/2007 |
| TW | 200906450 A | 2/2009 |

(Continued)

OTHER PUBLICATIONS

Zhang, Prog Materials Sci 49: 537-560 (2004).*
Third Chinese Office Action dated Jun. 28, 2013 in corresponding Chinese patent application No. 200980135720.6 (with partial English translation).
International Search Report dated Dec. 28, 2009 for the corresponding International patent application No. PCT/JP2009/004596.
Extended European Search Report dated Dec. 12, 2011 in corresponding European application No. 09814279.7.
Chinese Office Action dated May 17, 2012 in corresponding Chinese patent application No. 200980135720.6 (with English abstract).
Chinese Office Action dated Jan. 14, 2013 in corresponding Chinese patent application No. 200980135720.6 (with partial English translation).

(Continued)

*Primary Examiner* — Robert A Wax
*Assistant Examiner* — Thor Nielsen
(74) *Attorney, Agent, or Firm* — Posz Law Group, PLC

(57) ABSTRACT

The purpose of present invention is to provide a medicine which has low contamination with a fine-pulverizing medium, is safe and has improved bioavailability.
A method for producing a composite organic compound powder for medical use is used which comprises: mixing a poorly water-soluble and crystalline organic compound powder, a physiologically acceptable salt, a physiologically acceptable polyol, and a carboxyvinyl polymer and fine-pulverizing the organic compound powder; and removing at least the salt and the polyol during or after fine-pulverizing.

22 Claims, 4 Drawing Sheets

(56) References Cited

FOREIGN PATENT DOCUMENTS

WO        WO 9613178 A1 *   5/1996
WO        01/80828 A2    11/2001
WO        2007/007521 A1    1/2007

OTHER PUBLICATIONS

Russian Office Action dated Feb. 12, 2013 in corresponding Russian patent application No. 2011114292 (with English translation).
Office Action issued by the Patent Office of the Russian Federation dated Apr. 17, 2014 for the corresponding Russian Application No. 2011114292 (and English translation).

* cited by examiner

METHOD FOR PRODUCING A COMPOSITE ORGANIC COMPOUND POWDER FOR MEDICAL USE

CROSS REFERENCE TO RELATED APPLICATIONS

This application is a divisional of U.S. application Ser. No. 13/063,026 filed on Mar. 9, 2011, which is a U.S. national stage application of International Patent Application No. PCT/JP2009/004596 filed on Sep. 15, 2009 and is based on Japanese Patent Application No. 2008-241855 filed on Sep. 19, 2008, the disclosure of which is incorporated herein by reference.

TECHNICAL FIELD

The present invention relates to a composite organic compound powder for medical use containing poorly water-soluble organic compound particles, a method for producing the same, and a suspension in which the composite organic compound powder for medical use is dispersed.

BACKGROUND ART

Effective functioning of a medicinal ingredient in a formulation requires the reaching of the medicinal ingredient through blood vessels in the body to a target site. Capillaries, which are the narrowest among the blood vessels, are about 5 µm in diameter. Thus, in order for an organic compound with medicinal ingredients to pass through capillaries without causing occlusion, the organic compound needs to have a particle diameter of less than 5 µm.

Improved bioavailability for a formulation is very important in medical practice and pharmaceutical production because it reduces the dosage and thereby results in decreased side effects on the living body. Generally, the bioavailability for a formulation depends on the physicochemical properties, dosage form and route of administration of the drug. For example, while an oral formulation has the advantages of being convenient and causing little distress compared to an injectable (parenteral) preparation, it has the disadvantage of providing low bioavailability. The oral formulation enters the intestine through the stomach and duodenum, is absorbed mainly from the intestinal tract into the blood, and is transported to the liver through the portal vein. The oral formulation is partly decomposed by undergoing the action of gastric acid and the like or converted into a totally different substance by being metabolized in the liver during the course of passing through such a long route. One of the major reasons for the low bioavailability is that the oral formulation is less easily absorbed from digestive organs such as the intestine. To enhance the bioavailability for a formulation, it is necessary to decrease the size of the organic compound with medicinal ingredients to a level required to facilitate the absorption of the compound from the digestive organs into the blood.

Among formulations, more than a few contain a poorly water-soluble or water-insoluble organic compound as a medicinal ingredient. A formulation containing the poorly water-soluble or water-insoluble organic compound as a medicinal ingredient has previously been administered to the living body by decreasing the size of the organic compound using a method involving dissolving the organic compound in an organic solvent before dispensing, a method involving subjecting the organic compound to thermal dissolution before bringing the compound into emulsion (see e.g., Patent Literatures 1 and 2), a method involving converting the organic compound into fine grains having a size of the order of micron followed by mixing with water, or the like.

However, an organic solvent dissolving an organic compound can cause a medically undesirable event; thus, it is required to minimize the use of such an organic solvent. In addition, many of the organic compounds having medicinal ingredients each have almost the same melting point as the decomposition point thereof; thus, these organic compounds are liable to be decomposed at the same time as they are thermally dissolved and thereby to be changed into compounds incapable of being medicinal ingredients. Further, another problem is that it is difficult to use the method of thermal dissolution for organic compounds having high melting points.

With the recent progress of nanotechnology, attention has been drawn to a method for converting organic compounds into fine grains by finely pulverizing using mechanical means. For example, a method is known which involves fine-pulverizing a solid agrichemical active ingredient by a bead mill using beads composed of ceramic, glass, or the like (see e.g., Patent Literature 3). In addition, a method is also known which involves finely pulverizing an organic compound for use in ultraviolet absorbing agents using a pulverizing device such as a rotary ball mill (see e.g., Patent Literature 4). Further, a so-called solvent salt milling method, which is a method for finely pulverizing a pigment, is also known which involves subjecting crude dioxazine to wet fine-pulverizing in an inorganic salt and an organic liquid of an alcohol or a polyol (see e.g., Patent Literature 5).

CITATION LIST

Patent Literature

Patent Literature 1
Japanese Patent Laid-Open No. 2007-23051
Patent Literature 2
National Publication of International Patent Application No. 2003-531162
Patent Literature 3
Japanese Patent Laid-Open No. 2003-286105
Patent Literature 4
Japanese Patent Laid-Open No. H11-100317
Patent Literature 5
Japanese Patent Laid-Open No. H06-228454

SUMMARY OF INVENTION

Technical Problem

However, a fine-pulverizing method using a hard medium as in the bead mill and the rotary ball mill has a problem that when fine-pulverized, organic compound particles are contaminated with the hard medium and a wear powder generated from the worn-out mill container. In contrast, the solvent salt milling method uses a salt as a fine-pulverizing tool; thus, even if the salt is worn or crushed in fine-pulverizing organic compound particles, the salt can be washed away with water after fine-pulverizing. As a result, this method has the advantage of being less likely to pose a problem of contamination compared to the above fine-pulverizing method using a hard medium.

However, although the solvent salt milling method is useful as a method for fine-pulverizing organic pigments such as dioxazine and copper phthalocyanine, there is some question about the extent of g fine-pulverizing and as to whether it is a fine-pulverizing method applicable to organic compounds for medical use. In particular, organic compounds as active ingredients for pharmaceuticals are required to be fine-pulverized while keeping their crystal forms; however, since dissolution of such an organic compound in a medium liquid brings about dissolution and re-elution even with a trace amount, thereby resulting in a crystal form that is different from the form prior to fine-pulverizing, or an amorphous form, the selection of the medium liquid is known to be very difficult (Pharmaceutical Development and Technology, Vol. 9, No. 1, pp. 1-13 (2004)). Many of the organic pigments fine-pulverized by the solvent salt milling method are those developing a color due to the crystal structure, and their chemical structures each have fewer substituents and high molecular planarity, thus resulting in a compact crystal structure. As a result, many of the fine-pulverized materials are high melting point compounds (melting point: 350° C. or higher) and have the characteristic of low solubility in solvents. The solvent salt milling method is thought to be available because it is used for fine-pulverizing pigments having especially low solubility among other poorly soluble organic compounds. An organic compound for medical use often has significantly different characteristics such as a sparse crystalline lattice, a low melting point or high solubility in solvents compared to a pigment. When the method is applied to such an organic compound for medical use, the organic compound has been believed to be dissolved in the solvent and incapable of being finely pulverized.

Prior to the present invention, the present inventors attempted to pulverize finely an organic compound for medical use by mixing a salt therewith, and succeeded in finding a method capable of fine-pulverizing the compound to a level useful for a medicine. However, the following improvements are required in converting an organic compound for medical use into fine grains. That is, the following three points are required: 1) further enhancing a fine-pulverizing efficiency, 2) preventing the resultant fine grains from re-aggregating, and 3) preventing the reduction of the recovery rate of the nanonized organic compound for medical use. In addition to re-aggregation, the conversion of an organic compound for medical use into fine grains to a nano level may lead to the dissolution of the organic compound for medical use, even if poorly water-soluble, in washing water due to the increased specific surface area thereof. Generally, a poorly water-soluble substance is classified into two types: water-insoluble and very slightly water-soluble. The latter includes a substance capable of being dissolved when sufficient time is taken; this substance is classified as the poorly water-soluble substance when its dissolution time is so long that it is unsuitable for industrial use. On the other hand, an increase in the specific surface area due to the conversion into fine grains may increase the contacting surface with water and raise the dissolution rate.

Stably dispersed nanoparticles become very difficult to collect in the "filtration (separation)-washing step" because of their microscopic configuration. This is because they pass through a filter or the like in the filtration step and are not sufficiently precipitated in the centrifugation step. Thus, the high fine-pulverizing efficiency, high redispersibility and high collection efficiency represent mutually contradictory demands.

The present invention has been made to meet such demands and is intended to provide a medicine which has low contamination with a fine-pulverizing medium, is safe and has improved bioavailability.

Solution to Problem

As a result of intensive studies for solving the above-described problems, the present inventors have found that in addition to a physiologically acceptable salt and a physiologically acceptable polyol, a carboxyvinyl polymer can be added to an organic compound powder, followed by fine-pulverizing the mixture to pulverize the organic compound powder with a high efficiency, and that the salt and the polyol can be removed after fine-pulverizing to produce an organic compound powder which has an extremely small average particle diameter and a form in which the surface of each particle of the organic compound is partly or entirely covered by the carboxyvinyl polymer while keeping its crystal structure. Thereby, the present invention is accomplished. In addition, the present inventors have found that a lecithin can be added to the organic compound converted into grains, which is then subjected to mixing treatment to produce an organic compound powder rich in dispersibility and excellent in collection efficiency, thereby accomplishing the superior present invention. In this respect, the carboxyvinyl polymer can be added or not added in adding the lecithin.

Thus, the present invention relates to a composite organic compound powder for medical use which has the surface of particles of a poorly water-soluble and crystalline organic compound partly or entirely covered by a carboxyvinyl polymer and is 400 nm or less in the average particle diameter of the particles in a form covered by the carboxyvinyl polymer, converted from the BET specific surface area, to a suspension containing the powder, and to a fine-pulverizing method for obtaining the powder. The present invention also relates to a method for adding a lecithin to an organic compound converted into grains, followed by mixing treatment to produce a composite organic compound powder for medical use having an average particle diameter of 400 nm or less and a suspension containing the powder and to obtain the powder with high collection efficiency.

More specifically, the present invention is as follows.

(1) The composite organic compound powder for medical use according to the present invention has the surface of particles of a poorly water-soluble and crystalline organic compound partly or entirely covered by a carboxyvinyl polymer and is 400 nm or less in the average particle diameter of the particles in a form covered by the carboxyvinyl polymer, converted from the BET specific surface area.

(2) The organic compound is preferably one or more selected from the group consisting of fenofibrate, felbinac, pranlukast hydrate, miconazole, fluticasone propionate, indomethacin, amphotericin B, aciclovir, nifedipine, nicardipine, nimodipine, dipyridamole, disopyramide, prazosin hydrochloride, prednisolone, cortisone acetate, dexamethasone, betamethasone, beclometasone dipropionate, budesonide, fluocinolone acetonide, naproxen, ketoprofen, 7-(3, 5-dimethoxy-4-hydroxycinnamoylamino)-3-octyloxy-4-hydroxy-1-methyl-2(1H)-quinolinone, phenyloin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazine, phenprobamate, mequitazine, bisbentiamine, mitomycin C, bicalutamide, paclitaxel, ubenimex, dacarbazine, fluconazole, rifampicin, triamcinolone acetonide, clemastine fumarate, zafirlukast, dihydrocholesterol, β-carotene, propyl gallate, cinnamic acid, saccharin, folic acid, and maltol.

(3) The composite organic compound powder for medical use is preferably fenofibrate powder which is 50 to 400 nm in the average particle diameter converted from the BET specific surface area.

(4) The composite organic compound powder for medical use is also preferably felbinac powder which is 50 to 400 nm in the average particle diameter converted from the BET specific surface area.

(5) The composite organic compound powder for medical use is also preferably pranlukast hydrate powder which is 20 to 70 nm in the average particle diameter converted from the BET specific surface area.

(6) The composite organic compound powder for medical use is also preferably miconazole powder which is 50 to 300 nm in the average particle diameter converted from the BET specific surface area.

(7) The composite organic compound powder for medical use is also preferably fluticasone propionate powder which is 20 to 100 nm in the average particle diameter converted from the BET specific surface area.

(8) The composite organic compound powder for medical use is also preferably indomethacin powder which is 20 to 120 nm in the average particle diameter converted from the BET specific surface area.

(9) The composite organic compound powder for medical use according to the present invention further has a lecithin on the surface of the carboxyvinyl polymer or the organic compound particles.

(10) The present invention is a suspension in which the composite organic compound powder for medical use according to item (9) is dispersed.

(11) The method for producing a composite organic compound powder for medical use according to the present invention comprises: mixing a poorly water-soluble and crystalline organic compound powder, a physiologically acceptable salt, a physiologically acceptable polyol, and a carboxyvinyl polymer and fine-pulverizing the organic compound powder; and removing at least the salt and the polyol after fine-pulverizing.

(12) The method for producing a composite organic compound powder for medical use according to the present invention further comprises the step of adding a lecithin during or after fine-pulverizing.

(13) The organic compound powder is preferably one or more selected from the group consisting of fenofibrate, felbinac, pranlukast hydrate, miconazole, fluticasone propionate, indomethacin, amphotericin B, aciclovir, nifedipine, nicardipine, nimodipine, dipyridamole, disopyramide, prazosin hydrochloride, prednisolone, cortisone acetate, dexamethasone, betamethasone, beclometasone dipropionate, budesonide, fluocinolone acetonide, naproxen, ketoprofen, 7-(3,5-dimethoxy-4-hydroxycinnamoylamino)-3-octyloxy-4-hydroxy-1-methyl-2(1H)-quinolinone, phenyloin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazine, phenprobamate, mequitazine, bisbentiamine, mitomycin C, bicalutamide, paclitaxel, ubenimex, dacarbazine, fluconazole, rifampicin, triamcinolone acetonide, clemastine fumarate, zafirlukast, dihydrocholesterol, β-carotene, propyl gallate, cinnamic acid, saccharin, folic acid, and maltol.

(14) The salt is preferably one or more selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, and dipotassium hydrogen phosphate.

(15) The polyol is preferably glycerin, propylene glycol, or polyethylene glycol.

(16) The salt and the polyol are preferably sodium chloride and glycerin, respectively.

(17) The composite organic compound powder for medical use according to the present invention comprises composite particles in which a lecithin is carried on the surface of particles of a poorly water-soluble organic compound, or composite particles in which the organic compound and the lecithin form a composite at a nano level. The composite particles constituting the powder preferably have an average particle diameter of 400 nm or less as calculated in terms of volume.

(18) The organic compound is preferably one or more selected from the group consisting of fenofibrate, felbinac, pranlukast hydrate, miconazole, fluticasone propionate, indomethacin, amphotericin B, aciclovir, nifedipine, nicardipine, nimodipine, dipyridamole, disopyramide, prazosin hydrochloride, prednisolone, cortisone acetate, dexamethasone, betamethasone, beclometasone dipropionate, budesonide, fluocinolone acetonide, naproxen, ketoprofen, 7-(3,5-dimethoxy-4-hydroxycinnamoylamino)-3-octyloxy-4-hydroxy-1-methyl-2(1H)-quinolinone, phenyloin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazine, phenprobamate, mequitazine, bisbentiamine, mitomycin C, bicalutamide, paclitaxel, ubenimex, dacarbazine, fluconazole, rifampicin, triamcinolone acetonide, clemastine fumarate, zafirlukast, dihydrocholesterol, β-carotene, propyl gallate, cinnamic acid, saccharin, folic acid, and maltol.

(19) The composite organic compound powder for medical use is also preferably a powder of at least any one of amphotericin B, aciclovir and indomethacin having an average particle diameter of 50 to 250 nm.

(20) The present invention is also a suspension in which the composite organic compound powder for medical use according to at least any one of items (17) to (19) is dispersed.

(21) The method for producing a composite organic compound powder for medical use according to the present invention comprises: mixing a poorly water-soluble organic compound powder, a physiologically acceptable salt, and a physiologically acceptable polyol and fine-pulverizing the organic compound powder; and removing at least the salt and the polyol after fine-pulverizing.

(22) The method for producing the composite organic compound powder for medical use according to the present invention further comprises the step of adding a lecithin during or after fine-pulverizing.

According to the present invention, the "average particle diameter converted from the BET specific surface area" is calculated by converting a value of the specific surface area measured by the BET flow method (one-point type) to the diameter of a hypothetical spherical particle. The following formula 1 is a conversion formula for converting a value of the specific surface area to the diameter. Here, D is an average particle diameter, $\rho$ is a solid density, S is a specific surface area, and $\alpha$ is a shape factor. $\alpha$ is 6 for spherical particles.

$$D = \alpha/(\rho \cdot S) \qquad \text{(formula 1)}$$

The BET flow method is preferably a method for measuring the specific surface area by the following procedure. A mixed gas of nitrogen and helium is flowed into a cell in which a sample to be measured is placed, followed by cooling the sample with liquid nitrogen. Then, only nitrogen gas adsorbs to the surface of the sample. Subsequently, when the cell is returned to ordinary temperature, the desorption of the gas occurs. During the desorption of gas, the proportion of nitrogen gas in the mixed gas flowing through one detector becomes larger than the proportion of nitrogen gas flowing through another detector. The difference between signals from these detectors represents the adsorption amount, enabling the measurement of the specific surface area.

The "poorly water-soluble organic compound for medical use" according to the present invention preferably has a melting point of 80 to 400° C. The melting point of the poorly water-soluble organic compound for medical use according to the present invention is preferably 80 to 360° C., more preferably 80 to 320° C., most preferably 80 to 280° C.

For the purpose of the present specification, "poorly water-soluble" means that the solubility of an organic compound in water is low to such an extent that the compound is affected when used as a pharmaceutical, and as described above includes both the property of being insoluble in water and the property of being very slightly soluble. On the concept of poor water solubility in pharmaceuticals, a pharmacopeial description in each country may be referred to. For example, the solubility of a poorly water-soluble organic compound in water may be about 1 mg/mL or less at a common handling temperature for organic compounds for medical use, e.g., around the room temperature of 25° C.; it is preferably 0.5 mg/mL or less, more preferably 0.3 mg/mL, most preferably 0.1 mg/mL or less.

The "poorly water-soluble organic compound for medical use" according to the present invention is also preferably a crystalline poorly water-soluble organic compound for medical use. For the purpose of the present specification, "crystalline" is a form in which molecules are regularly arranged; whether or not a substance is crystalline can be examined using a method known to those skilled in the art, such as thermal analysis, X-ray diffraction, and electronic diffraction. The crystalline poorly water-soluble organic compound for medical use employed in the method of the present invention is also preferably an organic compound having a more distinct crystalline form. However, the "poorly water-soluble organic compound for medical use" also includes an amorphous organic compound without an essential requirement for being crystalline.

For the purpose of the present specification, the poorly water-soluble organic compound for medical use may be a natural product or a synthetic product. Examples of the natural product can include organic compounds derived from animals, organic compounds derived from plants, or organic compounds derived from microorganisms such as yeast. The poorly water-soluble organic compound for medical use according to the present invention may be one organic compound or a mixture of two or more organic compounds.

Examples of the poorly water-soluble organic compound for medical use can include fenofibrate, felbinac, pranlukast hydrate, miconazole, fluticasone propionate, indomethacin, amphotericin B, aciclovir, nifedipine, nicardipine, nimodipine, dipyridamole, disopyramide, prazosin hydrochloride, prednisolone, cortisone acetate, dexamethasone, betamethasone, beclometasone dipropionate, budesonide, fluocinolone acetonide, naproxen, ketoprofen, 7-(3,5-dimethoxy-4-hydroxycinnamoylamino)-3-octyloxy-4-hydroxy-1-methyl-2(1H)-quinolinone, phenyloin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazine, phenprobamate, mequitazine, bisbentiamine, mitomycin C, bicalutamide, paclitaxel, ubenimex, dacarbazine, fluconazole, rifampicin, triamcinolone acetonide, clemastine fumarate, zafirlukast, dihydrocholesterol, β-carotene, propyl gallate, cinnamic acid, saccharin, folic acid, and maltol; preferred are indomethacin, nifedipine, cortisone acetate, 7-(3,5-dimethoxy-4-hydroxycinnamoylamino)-3-octyloxy-4-hydroxy-1-methyl-2(1H)-quinolinone, miconazole, pranlukast, dexamethasone, and zafirlukast.

For the purpose of the present specification, "composition for medical use" is not particularly limited provided that it is used to treat, prevent or diagnose humans or animals. For example, the composition for medical use according to the present invention may be administered to the inside, surface or the like of the human or animal body, or used to treat a blood, a urea, or the like collected from a human or an animal outside the body. Examples of the composition for medical use can include an antipyretic agent, an analgesic agent, an anti-inflammatory agent, an antigout agent, a therapeutic agent for hyperuricemia, a hypnotic agent, a sedative agent, an anti-anxiety agent, an antipsychotic agent, an antidepressant, an antimanic agent, a psychostimulant, an antiepileptic agent, a muscle relaxant, a therapeutic agent for Parkinson's disease, an autonomic agent, a cerebral circulation and metabolism improver, a therapeutic agent for allergy, a cardiotonic agent, an antianginal agent, a beta blocker, a Ca-antagonist, an antiarrhythmic agent, an antidiuretic agent, a diuretic agent, a hypotensive agent, a therapeutic agent for peripheral circulation disorder, an agent for hyperlipidemia, a hypertensive agent, a respiratory stimulant, a bronchodilator, a therapeutic agent for asthma, an antitussive agent, an expectorant, a therapeutic agent for chronic obstructive pulmonary disease, a therapeutic agent for peptic ulcer, a purgative agent, an antidiarrheal/intestinal conditioner, an anti-diabetic agent, an adrenal cortical hormone preparation, a sex hormone preparation, an agent for osteoporosis, a bone metabolism improving agent, a vitamin preparation, a hematinic agent, a blood coagulant preparation, a chemotherapeutic agent, an antibiotic, an antifungal agent, an antiviral agent, an anticancer agent, an immunosuppressant, an ophthalmological drug, an otorhinolaryngological drug, an oral mucosal injury preparation, a dermatologic agent, radiopharmaceutical agent, a diagnostic agent, a lifestyle agent, and a herbal medicine.

According to the present invention, the carboxyvinyl polymer may have a form covering a part but not all of the particle surface of the poorly water-soluble and crystalline organic compound, or completely covering the particle surface. Also, according to the present invention, the lecithin may be present directly on the surface of the organic compound particle, or present on the surface of the carboxyvinyl polymer. For the purpose of the present specification, "physiologically acceptable" means being probably ingestible without any particular physiological problem; whether or not a substance is a physiologically acceptable substance is appropriately determined by the subject organism species of ingestion, the form of ingestion, and the like. Examples of the physiologically acceptable solvent include the substances approved as additives or solvents for pharmaceuticals or food products, and the like.

Advantageous Effects of Invention

According to the present invention, a medicine can be provided which has low contamination with a fine-pulverizing medium, is safe and has improved bioavailability.

DESCRIPTION OF EMBODIMENTS

Figure 1:
FIG. 1 is an SEM photograph (magnification: 10,000-fold) of the fine-pulverized powder of felbinac obtained under conditions of Example 2.

Embodiments of the composite organic compound powder for medical use and the production method and suspension of the same according to the present invention will now be described.

1. Composite Organic Compound Powder for Medical Use

The composite organic compound powder for medical use according to a preferable embodiment has the surface of particles of a poorly water-soluble and crystalline organic compound partly or entirely covered by a carboxyvinyl polymer and is 400 nm or less in the average particle diameter of the particles in a form covered by the carboxyvinyl polymer, converted from the BET specific surface area. In addition, the composite organic compound powder for medical use according to a preferable embodiment further has a lecithin on the surface of the carboxyvinyl polymer or the organic compound powder. Further, the composite organic compound powder for medical use according to this embodiment is particles in a form having a lecithin on the particle surface of the organic compound or in a form in which the organic compound and the lecithin form a composite, and also includes that having an average particle diameter of 400 nm or less as calculated in terms of volume.

(1) Organic Compound

Examples of the organic compound used in the composite organic compound powder for medical use include fenofibrate (melting point: 80 to 83° C.), felbinac (melting point: 163 to 166° C.), pranlukast hydrate (melting point: 231 to 235° C.), miconazole (melting point: 84 to 87° C.), fluticasone propionate (melting point: about 273° C. (decomposed)), indomethacin (melting point: 155 to 162° C.), nifedipine (melting point: 172 to 175° C.), nicardipine (melting point: 136 to 138° C.), nimodipine (melting point: 123 to 126° C.), dipyridamole (melting point: 165 to 169° C.), disopyramide (melting point: about 204° C.), prazosin hydrochloride (melting point: about 275° C. (decomposed)), prednisolone (melting point: about 235° C. (decomposed)), cortisone acetate (melting point: about 240° C. (decomposed)), dexamethasone (melting point: about 245° C. (decomposed)), betamethasone (melting point: about 240° C. (decomposed)), beclometasone dipropionate (melting point: about 208° C. (decomposed)), budesonide (melting point: about 240° C. (decomposed)), fluocinolone acetonide (melting point: about 266 to 274° C. (decomposed)), naproxen (melting point: 154 to 158° C.), ketoprofen (melting point: 94 to 97° C.), 7-(3,5-dimethoxy-4-hydroxycinnamoylamino)-3-octyloxy-4-hydroxy-1-methyl-2(1H)-quinolinone (hereinafter referred to as quinolinone derivative) (melting point: 186 to 187° C.), phenyloin (melting point: about 296° C. (decomposed)), phenacemide (melting point: 214 to 216° C.), ethotoin (melting point: 90 to 95° C.), primidone (melting point: 279 to 284° C.), diazepam (melting point: 130 to 134° C.), nitrazepam (melting point: about 227° C. (decomposed)), clonazepam (melting point: about 240° C. (decomposed)), digitoxin (melting point: about 256 to 257° C. (decomposed)), spironolactone (melting point: 198 to 207° C.), triamterene (melting point: 316° C.), chlorthalidone (melting point: 217° C.), polythiazide (melting point: 202.5° C.), benzthiazide (melting point: 231.5° C.), griseofulvin (melting point: 218 to 222° C.), nalidixic acid (melting point: 225 to 231° C.), chloramphenicol (melting point: 149 to 153° C.), chlorzoxazine (melting point: 188 to 192° C.), phenprobamate (melting point: 102 to 105.5° C.), mequitazine (melting point: 146 to 150° C.), bisbentiamine (melting point: 140 to 144° C.), triamcinolone acetonide (melting point: about 290° C. (decomposed)), fluconazole (melting point: 137 to 141° C.), rifampicin (melting point: 183 to 188° C. (decomposed)), dacarbazine (melting point: about 204° C. (decomposed)), mitomycin C (melting point: 300° C. or higher), bicalutamide (melting point: 190 to 195° C.), paclitaxel (melting point: 220 to 223° C.), ubenimex (melting point: about 234° C. (decomposed)), clemastine fumarate (melting point: 176 to 180° C. (decomposed)), erythromycin (melting point: 133 to 138° C.), amphotericin B (melting point: 170° C.), cefixime (melting point: about 240° C. (decomposed)), salazosulfapyridine (melting point: 240 to 249° C.), sparfloxacin (melting point: 266° C. (decomposed)), tinidazole (melting point: 125 to 129° C.), vidarabine (melting point: 248 to 254° C. (decomposed)), aciclovir (melting point: 300° C. (decomposed)), milrinone (melting point: about 317° C. (decomposed)), digoxin (melting point: about 230 to 265° C. (decomposed)), pindolol (melting point: 169 to 173° C.), propafenone hydrochloride (melting point: 172 to 175° C.), amrinone (melting point: about 297° C. (decomposed)), hydrochlorothiazide (melting point: 263 to 270° C. (decomposed)), trandolapril (melting point: 123 to 126° C.), candesartan cilexetil (melting point: 163.6 to 164.1° C. (decomposed)), urapidil (melting point: 156 to 161° C.), reserpine (melting point: 264 to 265° C. (decomposed)), methyldopa (melting point: 295 to 298° C. (decomposed)), norepinephrine (melting point: about 191° C. (decomposed)), simvastatin (melting point: 135 to 138° C.), fluoxymesterone (melting point: 270 to 278° C.), stanozolol (melting point: 230 to 242° C.), estradiol (melting point: 175 to 180° C.), chlormadinone acetate (melting point: 211 to 215° C.), falecalcitriol (melting point: about 143° C.), mazindol (melting point: 177 to 184° C. (decomposed)), sildenafil citrate (melting point: about 200 to 201° C.), minoxidil (melting point: 248° C.), droperidol (melting point: about 145 to 149° C.), quazepam (melting point: 148 to 151° C.), pentazocine (melting point: 154° C.), propericiazine (melting point: 113 to 118° C.), timiperone (melting point: 200 to 203° C.), sulpiride (melting point: 175 to 182° C.), amoxapine (melting point: 178 to 182° C. (decomposed)), lisuride maleate (melting point: about 195° C. (decomposed)), nicergoline (melting point: 134 to 138° C. (decomposed)), biperiden (melting point: 112 to 115° C.), levodopa (melting point: about 275° C. (decomposed)), chlorphenesin carbamate (melting point: 88 to 91° C.), dantrolene sodium (melting point: 200° C. or higher (decomposed)), formoterol fumarate (melting point: about 138° C. (decomposed)), atenolol (melting point: 153 to 156° C.), riluzole (melting point: about 118° C.), flumazenil (melting point: 198 to 202° C.), theophylline (melting point: 271 to 275° C. (decomposed)), methotrexate (melting point: 185 to 204° C. (decomposed)), amidotrizoic acid (melting point: 291 to 308° C. (decomposed)), cilostazol (melting point: 158 to 162° C.), adenine (melting point: about 360° C. (decomposed)), tolbutamide (melting point: 126 to 132° C.), famotidine (melting point: about 164° C. (decomposed)), ursodesoxycholic acid (melting point: 200 to 204° C.), sulindac (melting point: 180 to 187° C.), pirenoxine (melting point: about 245° C. (decomposed)), flunisolide (melting point: about 243° C. (decomposed)), danazol (melting point: 223 to 227° C. (decomposed)), and tacrolimus hydrate (melting point: about 130 to 133° C.). These organic compounds may use those produced by known methods.

(2) Carboxyvinyl Polymer

The carboxyvinyl polymer is an acrylic acid-based water-swellable vinyl polymer, and also known as a carbomer. Carbomers are not particularly limited provided that they are generally used in pharmaceuticals, and may be used alone or in a combination of two or more. Examples of the carbomer which may be used are a plurality of carbomers different in Mw, e.g., Carbopol (trademark) 934, Carbopol (trademark) 940, Carbopol (trademark) 980, Carbopol (trademark) 981, Carbopol (trademark) 2984, Carbopol (trademark) 5984, Carbopol (trademark) EDT 2050, Carbopol (trademark) Ultrez 10, HIVISWAKO (trademark) 103, HIVISWAKO (trademark) 104, and HIVISWAKO (trademark) 105.

(3) Lecithin

The lecithin is a compound consisting of a glycerin skeleton to which fatty acid residues and a phosphate group bonded to a basic compound or sugar are bonded, and also known as "phosphatidylcholine". Generally, a lecithin from soybean or rapeseed or from hen egg may be utilized. However, the type thereof is not particularly limited. The lecithin covers various types such as an oil-and-fat crude lecithin, a powdered high-purity lecithin obtained by delipidating the crude lecithin, a fractionated lecithin in which the ratio of a specific ingredient is increased using a solvent, a chromatography technique, and the like, a lecithin having oxidation stability increased by complete or partial hydrogenation followed by purification, and an enzymatically decomposed lecithin and an enzymatically modified lecithin obtained by enzymatically treating these lecithins; these lecithins may be all used.

2. Method for Producing Composite Organic Compound Powder for Medical Use

The method for producing the composite organic compound powder for medical use according to this embodiment comprises the steps of: mixing a poorly water-soluble and crystalline organic compound powder, a physiologically acceptable salt, a physiologically acceptable polyol, and a carboxyvinyl polymer and fine-pulverizing the organic compound powder; and removing the salt and the polyol after fine-pulverizing. The composite organic compound powder for medical use according to a preferable embodiment further comprises the step of adding a lecithin during or after fine-pulverizing. The method for producing the composite organic compound powder for medical use according to this embodiment also comprises the steps of mixing a poorly water-soluble organic compound powder, a physiologically acceptable salt, and a physiologically acceptable polyol and fine-pulverizing the organic compound powder; and removing at least the salt and the polyol after fine-pulverizing. In addition, this method preferably comprises the step of adding a lecithin during or after fine-pulverizing.

(1) Polyol

The polyol used in the production method according to the present embodiment is not particularly limited provided that it can be ingested without posing any particular physiological problem. The physiologically acceptable polyol is preferably that having low solubility in salt, that having high solubility in water, or that having a low freezing point and/or a high flash point. When the removal after fine-pulverizing is conveniently carried out, the physiologically acceptable polyol preferably has high solubility in water.

Examples of the polyol can include glycerin, propylene glycol, polyethylene glycol, dipropylene glycol, and diethylene glycol; preferred is propylene glycol or glycerin. The polyol preferably has a viscosity of 50 to 200,000 (dPa·S), more preferably 1,000 to 50,000 (dPa·S), still more preferably 5,000 to 30,000 (dPa·S).

The usage amount of the polyol is preferably 0.7 to 50 parts by mass, more preferably 2 to 15 parts by mass, still more preferably 3 to 10 parts by mass based on 1 part by mass of the organic compound to be fine-pulverized. The type of the polyol used may be appropriately determined in consideration of the solubility of the organic compound to be fine-pulverized. In addition, the polyols may be used alone or in a mixture of two or more thereof.

(2) Salt

The salt used in the production method according to the present embodiment is not particularly limited provided that it can be ingested without posing any particular physiological problem. The physiologically acceptable salt is preferably a salt having low solubility in the polyol, a salt having high solubility in water and/or a salt having low hygroscopicity and a hardness suitable for fine-pulverizing of the organic compound. The salt is more preferably a salt combining two or more of these properties. The solubility of the salt in the polyol is preferably 10 (mass/volume) % or less. When the removal of the salt after fine-pulverizing is conveniently carried out, the salt is preferably a salt having high solubility in water.

Examples of the preferable salt include sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate. Sodium chloride, potassium chloride, magnesium sulfate, calcium sulfate, sodium citrate, sodium dihydrogen phosphate, potassium dihydrogen phosphate, disodium hydrogen phosphate, dipotassium hydrogen phosphate, and the like may be mentioned, and preferred is sodium chloride.

The salt may also be subjected to the adjustment of its particle diameter by performing fine-pulverizing or the like before mixing with the poorly water-soluble organic compound for medical use. When the particle diameter of the salt is adjusted in advance, the volume average diameter of the particles may be, for example, 5 to 300 μm or 10 to 200 μm; however, it is preferably 0.01 to 300 μm, more preferably 0.1 to 100 μm, still more preferably 0.5 to 50 μm, most preferably 1 to 5 μm. The usage amount of the salt is preferably 1 to 100 parts by mass, more preferably 5 to 50 parts by mass, still more preferably 10 to 30 parts by mass based on 1 part by mass of the organic compound. In addition, the salts may be used alone or in a mixture of two or more thereof.

(3) Production Process

The composite organic compound powder for medical use according to the present embodiment is preferably produced through "fine-pulverizing step", "lecithin-mixing step", "filtration-washing step", and "drying step" in that order. However, the "fine-pulverizing step" and the "lecithin-mixing step" may also be carried out as one integrated step to mix the lecithin in fine-pulverized particles while fine-pulverizing. When the suspension containing a composite organic compound powder for medical use is produced, water is mixed with the composite organic compound powder for medical use obtained through the above steps, optionally after adding a dispersant. The "fine-pulverizing step", "lecithin-mixing step", "filtration (separation)-washing step", and "drying step" are described below.

(4) Fine-Pulverizing Step

In the production method according to the present embodiment, the fine-pulverizing device used for wet fine-pulverizing the organic compound may be used without any particular limitation provided that it has the ability to make the organic compound fine by a mechanical means. Examples of the fine-pulverizing device can include commonly used fine-pulverizing devices such as a kneader, a twin roll, a triple roll, a fret mill, a Hoover muller, a disk blade kneader-disperser, and a twin screw extruder.

To pulverize the organic compound finely, the organic compound, the salt and the carboxyvinyl polymer are preferably charged into a fine-pulverizing device and kneaded while slowly adding the polyol. The viscosity during kneading can be appropriately determined by the types of the organic compound to be fine-pulverized, the salt and the polyol. The temperature during fine-pulverizing can be appropriately determined in consideration of the organic compound to be fine-pulverized, the fine-pulverizing device, and the like. The temperature during fine-pulverizing is not particularly limited provided that it is a temperature capable of reducing the melting or decomposition of the organic compound; however, it is preferably −50 to 50° C., more preferably −20 to 30° C., most preferably −10 to 25° C. The fine-pulverizing time can be appropriately determined in consideration of the organic compound to be fine-pulverized, the fine-pulverizing device, and the like. The fine-pulverizing time may be, for example, 1 to 50 hours, and is preferably 3 to 30 hours, more preferably 5 to 20 hours, most preferably 6 to 18 hours.

The usage amount of the carboxyvinyl polymer is preferably 0.002 to 0.9 part by mass, more preferably 0.005 to 0.4 part by mass, still more preferably 0.03 to 0.07 part by mass based on 1 part by mass of the organic compound to be fine-pulverized. The type of the carboxyvinyl polymer used can be appropriately determined in consideration of the type of the organic compound to be fine-pulverized. In addition, the carboxyvinyl polymers may be used alone or in a mixture of two or more thereof having different Mw.

(5) Step of Mixing Lecithin

The lecithin is mixed with the kneaded matter being fine-pulverized or having been fine-pulverized. The kneaded matter may not contain the carboxyvinyl polymer. The mixing step may be carried out by mixing the lecithin after or during fine-pulverizing in the fine-pulverizing device and continuing the kneading in the same fine-pulverizing device. In addition, another device for mixing (a mixing device) may also be provided to transfer the kneaded matter after fine-pulverizing to the mixing device, followed by adding the lecithin thereto to perform the mixing step. The usage amount of the lecithin is preferably 0.01 to 10 parts by mass, more preferably 0.05 to 2 parts by mass, still more preferably 0.1 to 1.0 part by mass based on 1 part by mass of the organic compound to be fine-pulverized. The lecithin may be added alone; however, a mixture of the lecithin and the polyol may also be added. In the latter case, for the mixing ratio (weight ratio) of the lecithin and the polyol, the amount of the polyol is 1 to 10 parts by mass, more preferably 1.5 to 5 parts by mass, still more preferably 2 to 4 parts by mass based on 1 part by mass of the lecithin.

(6) Filtration (Separation)-Washing Step

After mixing the lecithin, filtration and washing are carried out to remove at least the salt and the polyol to provide a composite organic compound powder for medical use finely pulverized to a desired size. Specifically, the kneaded matter after mixing the lecithin can be placed in a solvent, which is then uniformly mixed using a homogenizer or the like, filtered, and washed with water to remove the salt and the polyol. The solvent used in uniformly mixing the kneaded matter is not particularly limited provided that it is a solvent in which the polyol and the salt are easily dissolved and the finely pulverized organic compound is hardly dissolved and which is physiologically acceptable. The solvent is preferably water; however, solvents other than water may also be used. Examples of the solvent other than water include a mixed solution of an organic solvent such as acetic acid, methanol and ethanol and water. The filtration method is not particularly limited, and may be a well-known method used to filter material containing an organic compound. Examples of the filtration method include a vacuum filtration method, a pressure filtration method, and an ultrafiltration membrane method. As a method for removing the salt and the polyol as does the filtration, a centrifugation method is available. A specific method of the centrifugation involves placing the lecithin-mixed kneaded matter in a solvent, which is then uniformly mixed using a homogenizer or the like, followed by precipitating the organic compound finely pulverized by the centrifuge and removing the supernatant. This operation can be repeated to remove the salt and the polyol. The electric conductivity of the supernatant can be measured to determine the end point of washing. That is, for example, if the electric conductivity of the supernatant is 10 μS/cm, then the concentration of sodium chloride can be estimated to be about 5 ppm; thus, the electric conductivity at the end point could be determined for adaptation to the characteristics of the substance.

Finely pulverized particles of the composite organic compound powder for medical use tend to aggregate because they generally have a high surface energy. Thus, an additive for preventing the secondary aggregation thereof may be added after removing the salt and the like. Examples of the secondary aggregation-preventing agent include alkyl sulfates, N-alkyloyl methyl taurine salts, ethanol, glycerin, propylene glycol, sodium citrate, purified soybean lecithin, phospholipids, D-sorbitol, lactose, xylitol, gum arabic, sucrose fatty acid esters, polyoxyethylene hydrogenated castor oil, polyoxyethylene fatty acid esters, polyoxyethylene glycol, polyoxyethylene sorbitan fatty acid esters, alkylbenzenesulfonates, sulfosuccinic acid ester salts, polyoxyethylene polyoxypropylene glycol, polyvinylpyrrolidone, polyvinyl alcohol, hydroxypropylcellulose, methylcellulose, hydroxyethylcellulose, hydroxypropylmethylcellulose, carmellose sodium, carboxyvinyl polymers, N-acylglutaminates, acrylate copolymers, methacrylate copolymers, casein sodium, L-valine, L-leucine, L-isoleucine, benzalkonium chloride, and benzethonium chloride. Alkylsulfates and N-alkyloyl methyl taurine salts are particularly preferable; among others, dodecyl sodium sulfate and N-myristoyl methyl taurine sodium are preferable. These secondary aggregation-preventing agents may be used alone or in a mixture of two or more thereof.

(7) Drying Method

After removing the salt and the polyol (referred to as "removing" when they are reduced even if not completely removed), drying treatment can be carried out to remove the solvent used for removing the salt and the like from the resultant composite organic compound powder for medical use. The drying method is not particularly limited, and may be a method conventionally used for drying organic compounds. Examples of the drying method include a vacuum drying method, a freeze-drying method, a spray drying method, and a freeze-spray drying method. The drying temperature or drying time for the process of drying is not particularly limited; however, the drying is preferably carried out at low temperature and preferably performed by a vacuum drying method, a freeze-drying method, a spray drying method, or a freeze-spray drying method to maintain the chemical stability of the composite organic compound particles for medical use and prevent the secondary aggregation of the particles.

3. Dosage Form

The fine particles constituting the composite organic compound powder for medical use obtained by the production method according to the present embodiment have an average particle diameter ranging preferably from 20 to 400 nm, more preferably from 20 to 300 nm or less, still more preferably from 50 to 150 nm as converted from the BET specific surface area.

The composite organic compound powder for medical use obtained by the production method according to the present embodiment is also excellent in formulation characteristics and can be used as a medicine in various dosage forms. For example, when the powder is used as an inhalant, a solvent-containing solid (hereinafter referred to as a wet cake) of the composite organic compound powder for medical use obtained by removing the salt and the polyol after fine-pulverizing can be suspended in water and adjusted in the form of porous particles about 1 to 30 μm in size by a freeze-spray drying method. To improve the dispersibility of the particles, a small amount of a surfactant may be added to the water. To similarly improve the dispersibility, a volatile additive such as ethanol may also be added in a small amount. When the volatile additive is added, irritation can be improved compared to when the surfactant is added because ethanol can be distilled off during drying.

When the composite organic compound powder for medical use is used in an injection, an eye-drop, an ointment, a percutaneous absorption agent, or the like, it can be used by adding a secondary aggregation-preventing agent to the wet cake to prepare a water dispersion. Examples of the secondary aggregation-preventing agent include a well-known surfactant. Specifically, the compounds may be used which have been listed in the place of the secondary aggregation-preventing agents capable of being added after removing the salt and the polyol. A water dispersion using a polymer such as an acrylate copolymer or a methacrylate copolymer as a secondary aggregation-preventing agent can be used as a DDS preparation. A water dispersion may also be prepared using a commonly used apparatus and the like. Examples of the apparatus include a homogenizer, a homomixer, an ultrasonic disperser, and a high-pressure homogenizer.

The water dispersion may also be powderized by vacuum drying, spray drying, freeze-drying, freeze-spray drying, or the like. The powder thus prepared is excellent in redispersibility in water; thus, it has excellent characteristics as an injection and an eye-drop prepared before use, and an oral agent.

The composite organic compound powder for medical use can also be dispersed in an oily substance to use the dispersion in ointments, capsules, percutaneous absorption preparations, and the like. The oily substance is not particularly limited provided that it is generally used in formulation. Examples of the oily substance include liquid paraffin, petrolatum, propylene glycol, glycerin, polyethylene glycol, and plant oil. These oily substances may be used alone or in a mixture of two or more thereof. The oily substance dispersion may be prepared using a commonly used apparatus and the like. Examples of the apparatus include a homogenizer, a homomixer, an ultrasonic disperser, a high-pressure homogenizer, a twin roll, a triple roll, a disk blade kneader-disperser, and a twin screw extruder.

EXAMPLES

The Examples of the present invention will now be described, comparing with Comparative Examples.

1. Fine-Pulverizing by Addition of Carboxyvinyl Polymer

Fine-pulverizing experiments are first described in each of which a carboxyvinyl polymer was added. The average particle diameter before and after fine-pulverizing for a dried powder was calculated by converting, by the above-described formula 1, the BET specific surface area measured using a BET type specific surface area analyzer (Macsorb model MH-1201, from Mountech Co., Ltd.). The observation of the powder before and after fine-pulverizing was carried out using a scanning electron microscope (model SEM VE-7800, from Keyence Corporation).

Example 1 Experiment of Fine-Pulverizing Fenofibrate

In a water-cooling type Hoover muller (from Imoto Seisakusho K.K.) were charged and uniformly mixed 0.1 g of fenofibrate with an average particle diameter of 6,640 nm (melting point: 80 to 83° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.36 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.073 g of a fine-pulverized powder with an average particle diameter of 338 nm.

Comparative Example 1: Experiment of Fine-Pulverizing Fenofibrate

Fenofibrate was fine-pulverized under the same conditions as in Example 1 except that a carboxyvinyl polymer was not added. As a result, 0.075 g of a fine-pulverized powder with an average particle diameter of 672 nm was obtained.

Example 2 Experiment of Fine-Pulverizing Felbinac

In a water-cooling type Hoover muller (from Imoto Seisakusho K.K.) were charged and uniformly mixed 0.1 g of felbinac with an average particle diameter of 34,000 nm (melting point: 163 to 166° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.33 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.081 g of a fine-pulverized powder with an average particle diameter of 207 nm.

Comparative Example 2: Experiment of Fine-Pulverizing Felbinac

In a water-cooling type Hoover muller (from Imoto Seisakusho K.K.) were charged and uniformly mixed 0.1 g of felbinac with an average particle diameter of 34,000 nm (melting point: 163 to 166° C.) and 1.6 g of fine-pulverized sodium chloride (average particle diameter: 5 μm), and the content was kept in a batter form by slowly adding dropwise 0.36 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.085 g of a fine-pulverized powder with an average particle diameter of 535 nm.

Example 3 Experiment of Fine-Pulverizing Pranlukast Hydrate

In a water-cooling type Hoover muller (from Imoto Seisakusho K.K.) were charged and uniformly mixed 0.1 g of pranlukast hydrate with an average particle diameter of 1,088 nm (melting point: about 231 to 235° C. (decomposed)), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.42 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.090 g of a fine-pulverized powder with an average particle diameter of 62 nm.

Comparative Example 3 Experiment of Fine-Pulverizing Pranlukast Hydrate

In a water-cooling type Hoover muller (from Imoto Seisakusho K.K.) were charged and uniformly mixed 0.1 g of pranlukast hydrate with an average particle diameter of 1,088 nm (melting point: about 231 to 235° C. (decomposed)) and 1.6 g of fine-pulverized sodium chloride (average particle diameter: 5 μm), and the content was kept in a batter form by slowly adding dropwise 0.36 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.098 g of a fine-pulverized powder with an average particle diameter of 73 nm.

Example 4 Experiment of Fine-Pulverizing Miconazole

In a water-cooling type Hoover muller (from Imoto Seisakusho K.K.) were charged and uniformly mixed 0.1 g of miconazole with an average particle diameter of 10,900 nm (melting point: 84 to 87° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.345 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.058 g of a fine-pulverized powder with an average particle diameter of 142 nm.

Comparative Example 4 Experiment of Fine-Pulverizing Miconazole

In a water-cooling type Hoover muller (from Imoto Seisakusho K.K.) were charged and uniformly mixed 0.1 g of miconazole with an average particle diameter of 10,900 nm (melting point: 84 to 87° C.) and 1.6 g of fine-pulverized sodium chloride (average particle diameter: 5 μm), and the content was kept in a batter form by slowly adding dropwise 0.33 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.060 g of a fine-pulverized powder with an average particle diameter of 358 nm.

Example 5 Experiment of Fine-Pulverizing Fluticasone Propionate

In a water-cooling type Hoover muller (from Imoto Seisakusho K.K.) were charged and uniformly mixed 0.1 g of fluticasone propionate with an average particle diameter of 7,850 nm (melting point: about 273° C. (decomposed)), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.375 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.071 g of a fine-pulverized powder with an average particle diameter of 71 nm.

Comparative Example 5 Experiment of Fine-Pulverizing Fluticasone Propionate

In a water-cooling type Hoover muller (from Imoto Seisakusho K.K.) were charged and uniformly mixed 0.1 g of fluticasone propionate with an average particle diameter of 7,850 nm (melting point: about 273° C. (decomposed)) and 1.6 g of fine-pulverized sodium chloride (average particle diameter: 5 μm), and the content was kept in a batter form by slowly adding dropwise 0.33 g of glycerin and fine-pulverized by kneading for 100 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.075 g of a fine-pulverized powder with an average particle diameter of 114 nm.

Example 6 Experiment of Fine-Pulverizing Indomethacin

In a 0.2-L kneader (destructive type kneader, from Yoshida Seisakusho Co., Ltd.) were charged and uniformly mixed 8 g of indomethacin with an average particle diameter of 3,960 nm (melting point: 155 to 162° C.), 170 g of fine-pulverized sodium chloride (average particle diameter: 5 μm), and 0.5 g of a carboxyvinyl polymer (Carbopol 980, from Nikko Chemicals Co., Ltd.), and the content was kept in a batter form by slowly adding dropwise 36 g of glycerin and fine-pulverized at 5° C. for 10 hours. Thereafter, the content was placed in 1 L of a 0.1 mol/L aqueous solution of acetic acid, uniformly dispersed using a homogenizer and then filtered and washed with water; the resultant wet cake was dried under reduced pressure at 30° C. to provide 7 g of a fine-pulverized powder of indomethacin with an average particle diameter of 58.5 nm.

Comparative Example 6 Experiment of Fine-Pulverizing Indomethacin

In a 0.2-L kneader (destructive type kneader, from Yoshida Seisakusho Co., Ltd.) were charged and uniformly mixed 8 g of indomethacin with an average particle diameter of 3,960 nm (melting point: 155 to 162° C.) and 170 g of fine-pulverized sodium chloride (average particle diameter: 5 μm), and the content was kept in a batter form by slowly adding dropwise 35.5 g of glycerin and fine-pulverized at 5° C. for 8 hours. Thereafter, the content was placed in 1 L of a 0.1 mol/L aqueous solution of acetic acid, uniformly dispersed using a homogenizer and then filtered and washed with water; the resultant wet cake was dried under reduced pressure at 30° C. to provide 7 g of a fine-pulverized powder of indomethacin with an average particle diameter of 141 nm.

Figure 2:
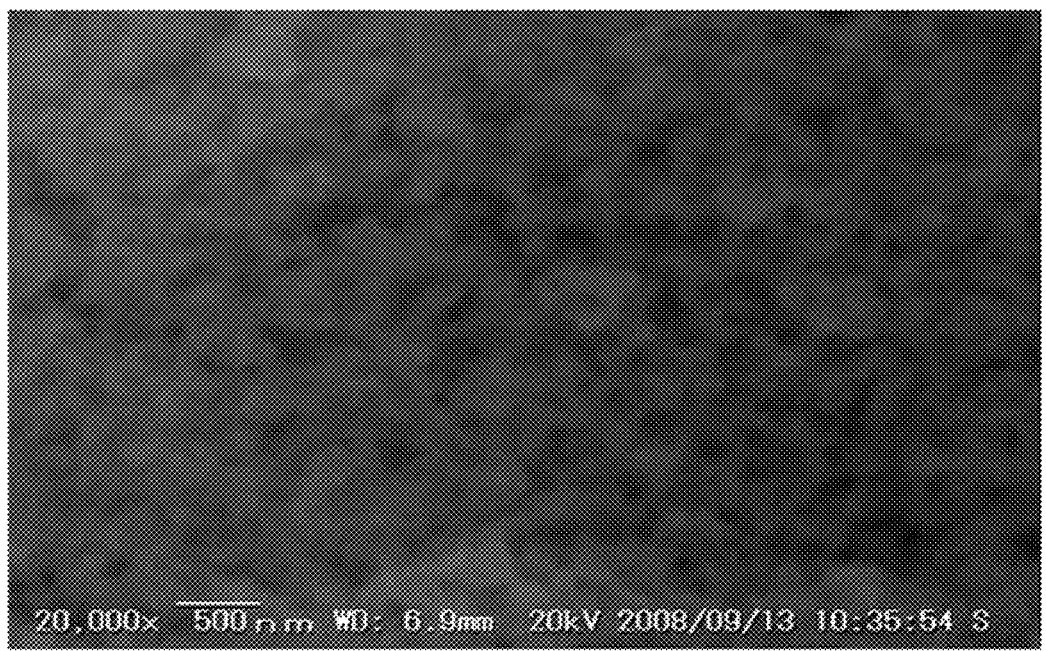
FIG. 2 is an SEM photograph in which a part of the field of view shown in FIG. 1 is enlarged (magnification: 20,000-fold).
Figure 3:
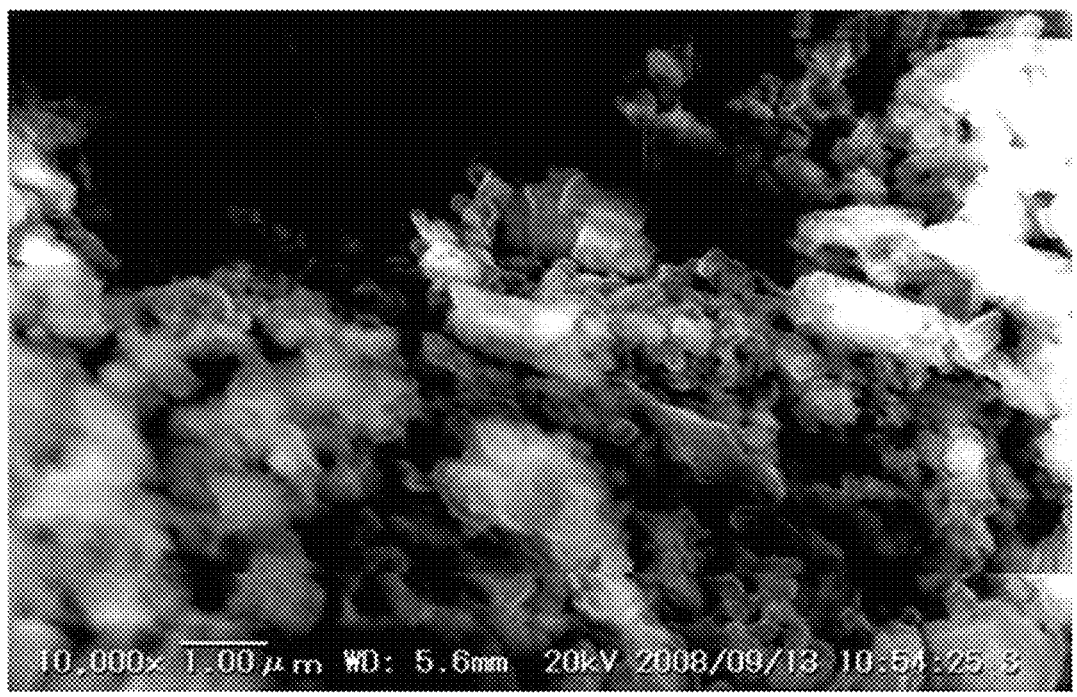
FIG. 3 is an SEM photograph (magnification: 10,000-fold) of the fine-pulverized powder of felbinac obtained under conditions of Comparative Example 2.
Figure 4:
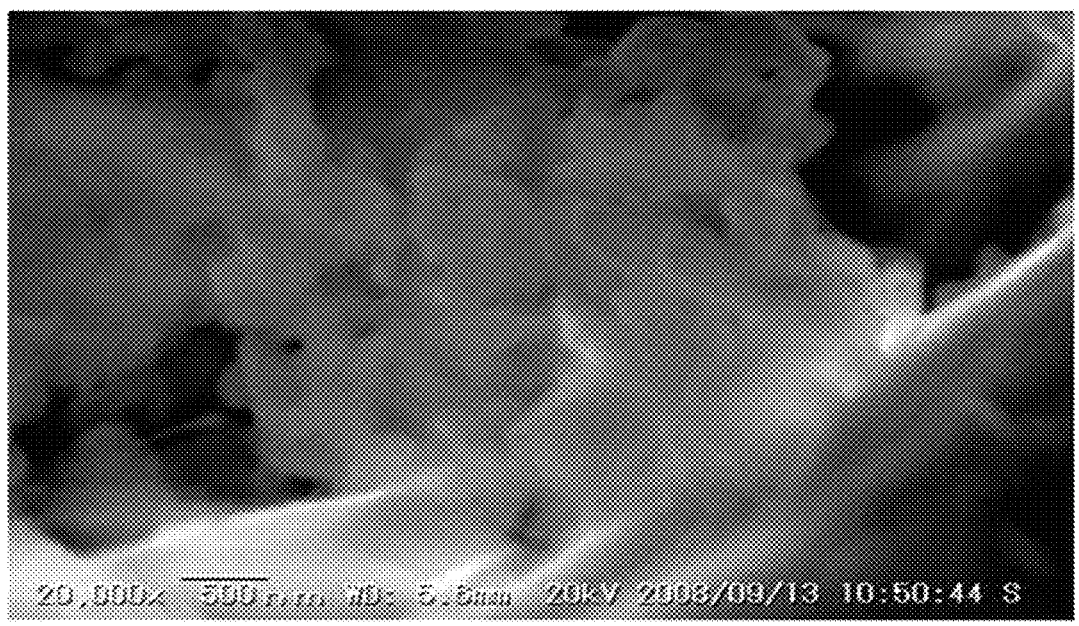
FIG. 4 is an SEM photograph in which a part of the field of view shown in FIG. 3 is enlarged (magnification: 20,000-fold).
Figure 5:
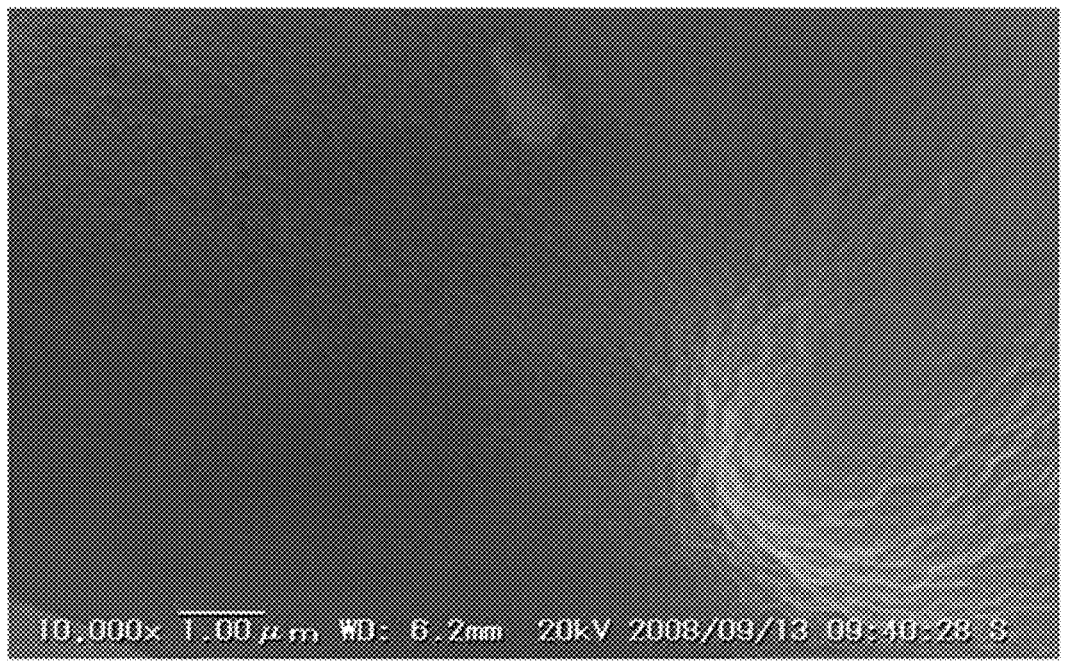
FIG. 5 is an SEM photograph (magnification: 10,000-fold) of the fine-pulverized powder of fluticasone propionate obtained under conditions of Example 5.
Figure 6:
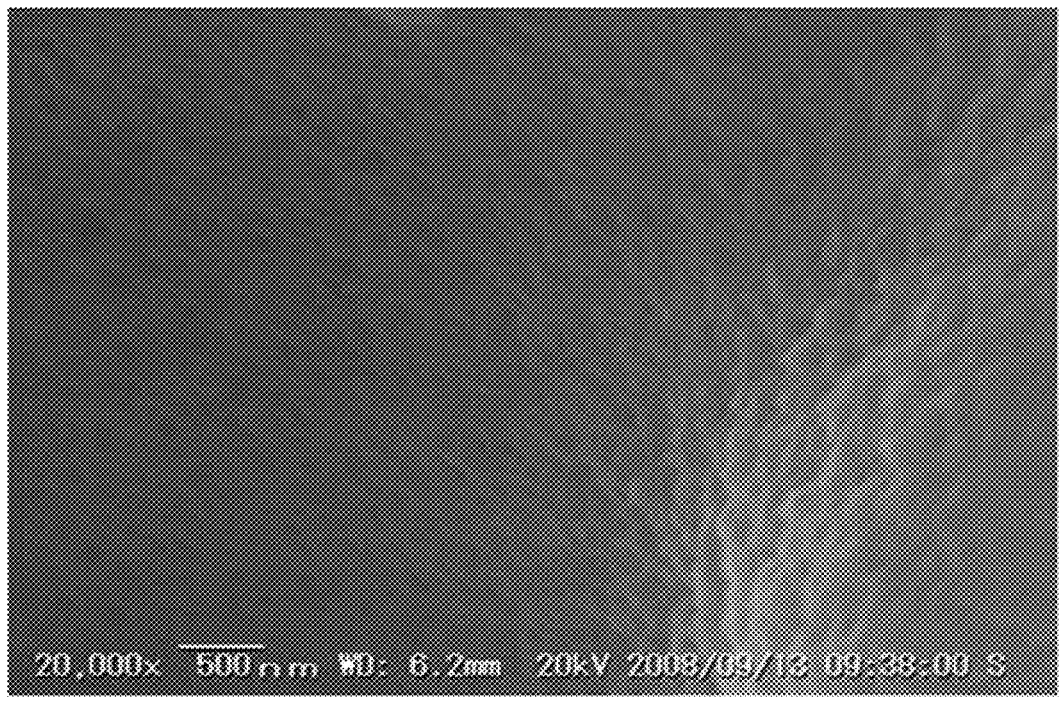
FIG. 6 is an SEM photograph in which a part of the field of view shown in FIG. 5 is enlarged (magnification: 20,000-fold).
Figure 7:
FIG. 7 is an SEM photograph (magnification: 10,000-fold) of the fine-pulverized powder of fluticasone propionate obtained under conditions of Comparative Example 5.
Figure 8:
FIG. 8 is an SEM photograph in which a part of the field of view shown in FIG. 7 is enlarged (magnification: 20,000-fold).

Table 1 shows the results of Examples 1 to 6 and Comparative Examples 1 to 6. FIGS. 1 and 2 show an SEM photograph (magnification: 10,000-fold) of the fine-pulverized powder of felbinac obtained in Example 2 and the magnified part (magnification: 20,000-fold) of the SEM photograph, respectively; FIGS. 3 and 4 show an SEM photograph (magnification: 10,000-fold) of the fine-pulverized powder of felbinac obtained in Comparative Example 2 and the magnified part (magnification: 20,000-fold) of the SEM photograph, respectively; FIGS. 5 and 6 show an SEM photograph (magnification: 10,000-fold) of the fine-pulverized powder of fluticasone propionate obtained in Example 5 and the magnified part (magnification: 20,000-fold) of the SEM photograph, respectively; and FIGS. 7 and 8 show an SEM photograph (magnification: 10,000-fold) of the fine-pulverized powder of fluticasone propionate obtained in Comparative Example 5 and the magnified part (magnification: 20,000-fold) of the SEM photograph, respectively.

As shown in Table 1, the fine-pulverizing of each pharmaceutical organic compound under the addition of the carboxyvinyl polymer evidently reduced the average particle diameter of the compound. Comparison between FIGS. 1 and 3 (or FIGS. 2 and 4) and between FIGS. 5 and 7 (or FIGS. 6 and 8) shows that the powders fine-pulverized under the addition of the carboxyvinyl polymer had smaller diameters than those of the powders fine-pulverized without adding the carboxyvinyl polymer. These comparative results of the SEM photographs also agree with the data shown in Table 1.

TABLE 1

| | Organic Compound | Average Particle Diameter before Fine-pulverizing (nm) | Average Particle Diameter after Fine-pulverizing (nm) |
|---|---|---|---|
| Example 1 | Fenofibrate | 6,640 | 338 |
| Example 2 | Felbinac | 34,000 | 207 |
| Example 3 | Pranlukast Hydrate | 1,088 | 62 |
| Example 4 | Miconazole | 10,900 | 142 |
| Example 5 | Fluticasone Propionate | 7,850 | 71 |
| Example 6 | Indomethacin | 3,960 | 59 |
| Comp. Example 1 | Fenofibrate | 6,640 | 672 |
| Comp. Example 2 | Felbinac | 34,000 | 535 |
| Comp. Example 3 | Pranlukast Hydrate | 1,088 | 73 |
| Comp. Example 4 | Miconazole | 10,900 | 358 |
| Comp. Example 5 | Fluticasone Propionate | 7,850 | 114 |
| Comp. Example 6 | Indomethacin | 3,960 | 141 |

2. Fine-Pulverizing by Addition of Carboxyvinyl Polymer and Lecithin

Fine-pulverizing experiments will now be described in each of which a carboxyvinyl polymer and a lecithin were added. The average particle diameter before and after fine-pulverizing for a powder was measured using a BET type specific surface area analyzer (Macsorb model HM-1201, from Mountech Co., Ltd.). The particle diameter of particles in a suspension was measured using a particle size distribution analyzer (Delsa Nano S, from Beckman Coulter, Inc.). "$D_{50}$" is the diameter of a particle having an integrated value of 50% as counted in order of decreasing particle size (or in order of increasing particle size) (called "median particle diameter") in the size distribution. "$D_{90}$" is the diameter of a particle having an integrated value of 90% as counted in order of increasing particle size (called "90% median diameter") in the size distribution. "$D_v$" is the volume average diameter (called "average particle diameter").

Example 7 Experiment of Fine-Pulverizing Fenofibrate

In a water-cooling type Hoover muller (from Imoto Seisakusho K.K.) were charged and uniformly mixed 0.1 g of fenofibrate with an average particle diameter of 6,640 nm (melting point: 80 to 83° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.36 g of glycerin and fine-pulverized by kneading for 100 cycles at 20° C. In addition, 0.1 g of a purified hydrogenated soybean lecithin-glycerin mixture (weight ratio: 1:3) was uniformly mixed in the resultant fine-pulverized and kneaded matter, which was then kneaded for 50 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.094 g of a powder. Subsequently, 5 g of 1% dodecyl sodium sulfate was added as a dispersant to 0.05 g of the resultant fenofibrate-containing powder and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 159.2 nm, a median particle diameter ($D_{50}$) of 135.1 nm, and a 90% median diameter ($D_{90}$) of 199.6 nm.

Comparative Example 7 Experiment of Fine-Pulverizing Fenofibrate

To 0.05 g of the powder produced in Example 1 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 556.5 nm, a median particle diameter ($D_{50}$) of 457.2 nm, and a 90% median diameter ($D_{90}$) of 742.6 nm.

Comparative Example 8 Experiment of Fine-Pulverizing Fenofibrate

To 0.05 g of the powder produced in Comparative Example 1 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 629.5 nm, a median particle diameter ($D_{50}$) of 893.6 nm, and a 90% median diameter ($D_{90}$) of 1,867 nm.

Example 8 Experiment of Fine-Pulverizing Felbinac

In a water-cooling type Hoover muller (from Imoto Seisakusho K.K.) were charged and uniformly mixed 0.1 g of felbinac with an average particle diameter of 34,000 nm (melting point: 163 to 166° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.33 g of glycerin and fine-pulverized by kneading for 100 cycles at 20° C. In addition, 0.1 g of a purified hydrogenated soybean lecithin-glycerin mixture (weight ratio: 1:3) was uniformly mixed in the resultant fine-pulverized and kneaded matter, which was then kneaded for 50 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.106 g of a powder. Subsequently, 5 g of 1% N-myristoyl methyl taurine sodium was added as a dispersant to 0.05 g of the resultant felbinac-containing powder and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 147.1 nm, a median particle diameter ($D_{50}$) of 121.5 nm, and a 90% median diameter ($D_{90}$) of 192.3 nm.

Comparative Example 9 Experiment of Fine-Pulverizing Felbinac

To 0.05 g of the powder produced in Example 2 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 5,618 nm, a median particle diameter ($D_{50}$) of 273.0 nm, and a 90% median diameter ($D_{90}$) of 10,321 nm.

Comparative Example 10 Experiment of Fine-Pulverizing Felbinac

To 0.05 g of the powder produced in Comparative Example 2 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 610.8 nm, a median particle diameter ($D_{50}$) of 498.2 nm, and a 90% median diameter ($D_{90}$) of 842.8 nm.

Example 9 Experiment of Fine-Pulverizing Pranlukast Hydrate

In a water-cooling type Hoover muller (from Imoto Seisakusho K.K.) were charged and uniformly mixed 0.1 g of pranlukast hydrate with an average particle diameter of 1,088 nm (melting point: about 231 to 235° C. (decomposed)), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.42 g of glycerin and fine-pulverized by kneading for 100 cycles at 20° C. In addition, 0.2 g of a purified hydrogenated soybean lecithin-glycerin mixture (weight ratio: 1:3) was uniformly mixed in the resultant fine-pulverized and kneaded matter, which was then kneaded for 50 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.119 g of a powder. Subsequently, 5 g of 1% dodecyl sodium sulfate was added as a dispersant to 0.05 g of the resultant pranlukast hydrate-containing powder and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 105.3 nm, a median particle diameter ($D_{50}$) of 89.9 nm, and a 90% median diameter ($D_{90}$) of 131.7 nm.

Comparative Example 11 Experiment of Fine-Pulverizing Pranlukast Hydrate

To 0.05 g of the powder produced in Example 3 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 43,804 nm, a median particle diameter ($D_{50}$) of 38,306 nm, and a 90% median diameter ($D_{90}$) of 39,845 nm.

Comparative Example 12 Experiment of Fine-Pulverizing Pranlukast Hydrate

To 0.05 g of the powder produced in Comparative Example 3 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 50,510 nm, a median particle diameter ($D_{50}$) of 46,227 nm, and a 90% median diameter ($D_{90}$) of 59,856 nm.

Example 10 Experiment of Fine-Pulverizing Miconazole

In a water-cooling type Hoover muller (from Imoto Seisakusho K.K.) were charged and uniformly mixed 0.1 g of miconazole with an average particle diameter of 10,900 nm (melting point: 84 to 87° C.), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.345 g of glycerin and fine-pulverized by kneading for 100 cycles at 20° C. In addition, 0.1 g of a purified hydrogenated soybean lecithin-glycerin mixture (weight ratio: 1:3) was uniformly mixed in the resultant fine-pulverized and kneaded matter, which was then kneaded for 50 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.075 g of a powder. Subsequently, 5 g of 1% dodecyl sodium sulfate was added as a dispersant to 0.05 g of the resultant miconazole-containing powder and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 144.9 nm, a median particle diameter ($D_{50}$) of 126.5 nm, and a 90% median diameter ($D_{90}$) of 182 nm.

Comparative Example 13 Experiment of Fine-Pulverizing Miconazole

To 0.05 g of the powder produced in Example 4 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 155.5 nm, a median particle diameter ($D_{50}$) of 136 nm, and a 90% median diameter ($D_{90}$) of 193.6 nm.

Comparative Example 14 Experiment of Fine-Pulverizing Miconazole

To 0.05 g of the powder produced in Comparative Example 4 was added 5 g of 1% dodecyl sodium sulfate as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 20,059 nm, a median particle diameter ($D_{50}$) of 17,562 nm, and a 90% median diameter ($D_{90}$) of 22,729 nm.

Example 11 Experiment of Fine-Pulverizing Fluticasone Propionate

In a water-cooling type Hoover muller (from Imoto Seisakusho K.K.) were charged and uniformly mixed 0.1 g of fluticasone propionate with an average particle diameter of 7,850 nm (melting point: about 273° C. (decomposed)), 1.6 g of fine-pulverized sodium chloride (average particle diameter: 5 μm), and 0.005 g of a carboxyvinyl polymer (Carbopol 980, from Nikko Chemicals Co., Ltd.), and the content was kept in a batter form by slowly adding dropwise 0.375 g of glycerin and fine-pulverized by kneading for 100 cycles at 20° C. In addition, 0.15 g of a purified hydrogenated soybean lecithin-glycerin mixture (weight ratio: 1:3) was uniformly mixed in the resultant fine-pulverized and kneaded matter, which was then kneaded for 50 cycles at 20° C. Thereafter, the content was placed in 50 mL of a 0.1 mol/L aqueous solution of acetic acid, uniformly dispersed using an ultrasonic apparatus (UT-105, from Sharp Manufacturing System Corporation) and then filtered and washed with water; the resultant wet cake was dried under reduced pressure at 30° C. to provide 0.092 g of a powder. Subsequently, 5 g of 1% N-myristoyl methyl taurine sodium was added as a dispersant to 0.05 g of the resultant fluticasone propionate-containing powder and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 96 nm, a median particle diameter ($D_{50}$) of 79 nm, and a 90% median diameter ($D_{90}$) of 127.2 nm.

Comparative Example 15 Experiment of Fine-Pulverizing Fluticasone Propionate To 0.05 g of the powder produced in Example 5 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 902.3 nm, a median particle diameter ($D_{50}$) of 126.2 nm, and a 90% median diameter ($D_{90}$) of 2,129 nm.

Comparative Example 16 Experiment of Fine-Pulverizing Fluticasone Propionate To 0.05 g of the powder produced in Comparative Example 5 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 3,508 nm, a median particle diameter ($D_{50}$) of 3,315 nm, and a 90% median diameter ($D_{90}$) of 4,406 nm.

Example 12 Experiment of Fine-Pulverizing Indomethacin

In a 0.2-L kneader (destructive type kneader, from Yoshida Seisakusho Co., Ltd.) were charged and uniformly mixed 8 g of indomethacin with an average particle diameter of 3,960 nm (melting point: 155 to 162° C.), 170 g of fine-pulverized sodium chloride (average particle diameter: 5 μm), and 0.5 g of a carboxyvinyl polymer, and the content was kept in a batter form by slowly adding dropwise 39 g of glycerin and fine-pulverized at 5° C. for 10 hours. Subsequently, 16 g of a purified hydrogenated soybean lecithin-glycerin mixture (weight ratio: 1:3) and 23 g of glycerin were uniformly mixed in the resultant fine-pulverized and kneaded matter, which was then kneaded at 10° C. for one hour. Thereafter, the content was placed in 1 L of a 0.1 mol/L aqueous solution of acetic acid, uniformly dispersed using a homogenizer and then filtered and washed with water; the resultant wet cake was dried under reduced pressure at 30° C. to provide 11.1 g of a powder. Then, 5 g of 1% N-myristoyl methyl taurine sodium was added as a dispersant to 0.05 g of the resultant indomethacin-containing powder and uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 103 nm, a median particle diameter ($D_{50}$) of 83.9 nm, and a 90% median diameter ($D_{90}$) of 139.2 nm.

Comparative Example 17 Experiment of Fine-Pulverizing Indomethacin

To 0.05 g of the powder produced in Example 6 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 123.7 nm, a median particle diameter ($D_{50}$) of 99.7 nm, and a 90% median diameter ($D_{90}$) of 166.3 nm.

Comparative Example 18 Experiment of Fine-Pulverizing Indomethacin

To 0.05 g of the powder produced in Comparative Example 6 was added 5 g of 1% N-myristoyl methyl taurine sodium as a dispersant, which was then uniformly dispersed using an ultrasonic apparatus (UT-105, from Sharp Manufacturing System Corporation). To the dispersion was added 44.95 g of purified water to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 319.9 nm, a median particle diameter ($D_{50}$) of 238.3 nm, and a 90% median diameter ($D_{90}$) of 461.5 nm.

Table 2 shows the results of Examples 7 to 12 and Comparative Examples 7 to 18. As shown in Table 2, the powders prepared by adding the carboxyvinyl polymer and the lecithin had a high redispersibility in water and a smaller average particle diameter in suspensions thereof. In contrast, the powders prepared without adding any lecithin have proved to be difficult to disperse sufficiently in suspensions thereof.

TABLE 2

| | Organic Compound | Average Particle Diameter before Fine-pulverizing (nm) | Diameter of Particle in Suspension (nm) | | |
|---|---|---|---|---|---|
| | | | Dv | D50 | D90 |
| Example 7 | Fenofibrate | 6,640 | 159 | 135 | 200 |
| Example 8 | Felbinac | 34,000 | 147 | 122 | 192 |
| Example 9 | Pranlukast Hydrate | 1,088 | 105 | 90 | 132 |
| Example 10 | Miconazole | 10,900 | 145 | 127 | 182 |
| Example 11 | Fluticasone Propionate | 7,850 | 96 | 79 | 127 |
| Example 12 | Indomethacin | 3,960 | 103 | 84 | 139 |
| Comp. Example 7 | Fenofibrate | 6,640 | 557 | 457 | 743 |
| Comp. Example 8 | Fenofibrate | 6,640 | 630 | 894 | 1,867 |
| Comp. Example 9 | Felbinac | 34,000 | 5,618 | 273 | 10,321 |
| Comp. Example 10 | Felbinac | 34,000 | 611 | 498 | 843 |
| Comp. Example 11 | Pranlukast Hydrate | 1,088 | 43,804 | 38,306 | 39,845 |
| Comp. Example 12 | Pranlukast Hydrate | 1,088 | 50,510 | 46,227 | 59,856 |
| Comp. Example 13 | Miconazole | 10,900 | 156 | 136 | 194 |
| Comp. Example 14 | Miconazole | 10,900 | 20,059 | 17,562 | 22,729 |
| Comp. Example 15 | Fluticasone Propionate | 7,850 | 902 | 126 | 2,129 |
| Comp. Example 16 | Fluticasone Propionate | 7,850 | 3,508 | 3,315 | 4,406 |
| Comp. Example 17 | Indomethacin | 3,960 | 124 | 100 | 166 |
| Comp. Example 18 | Indomethacin | 3,960 | 320 | 238 | 462 |

3. Improvement of Collection Efficiency by Addition of Lecithin

An experiment of improving a collection efficiency by addition of a lecithin to fine-pulverized particles will now be described. Unless otherwise stated, the average particle diameter of particles was measured using a BET type specific surface area analyzer (Macsorb model HM-1201, from Mountech Co., Ltd.). The particle diameter of particles in a suspension was measured using a particle size distribution analyzer (Delsa Nano S, from Beckman Coulter, Inc.). "$D_{50}$" is the diameter of a particle having an integrated value of 50% as counted in order of decreasing particle size (or in order of increasing particle size) (called "median particle diameter") in the size distribution. "$D_{90}$" is the diameter of a particle having an integrated value of 90% as counted in order of increasing particle size (called "90% median diameter") in the size distribution. "$D_v$" is the volume average diameter (called "average particle diameter").

Example 13 Experiment of Fine-Pulverizing and Collecting Amphotericin B

In a water-cooling type Hoover muller (from Imoto Seisakusho K.K.) were charged and uniformly mixed 0.1 g of amphotericin B with an average particle diameter of 13,423 nm (melting point: decomposed at 170° C. or higher) and 1.6 g of fine-pulverized sodium chloride (average particle diameter: 5 μm), and the content was kept in a batter form by slowly adding dropwise 0.36 g of glycerin and fine-pulverized by kneading for 100 cycles at 20° C.

Here, the average amphotericin B particle diameter of 13,423 nm before fine-pulverizing is a value measured in the following manner. Five grams of 0.03% sodium lauryl sulfate was added as a dispersant to 0.01 g of amphotericin B and uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 13,423 nm, a median particle diameter ($D_{50}$) of 11,843 nm, and a 90% median diameter ($D_{90}$) of 15,181 nm.

In the fine-pulverized and kneaded matter obtained by fine-pulverizing using the water-cooling type Hoover muller (from Imoto Seisakusho K.K.) was uniformly mixed 0.1 g of a purified hydrogenated soybean lecithin-glycerin mixture (weight ratio: 1:3), which was then kneaded in an agate mortar. Thereafter, the content was placed in 50 mL of a 0.1 mol/L aqueous solution of acetic acid, uniformly dispersed using an ultrasonic apparatus (UT-105, from Sharp Manufacturing System Corporation) and then centrifuged (at 6,000 rpm for 10 minutes, using CN-2060 from AS ONE Corporation), followed by removing the supernatant. This operation was performed four times, and a wet cake was then obtained. To 512 mg of the wet cake was added 3 g of purified water, which was then uniformly dispersed using the ultrasonic apparatus (UT-105, from Sharp Manufacturing System Corporation) to provide 3.5 g of a suspension. The size distribution of the resultant suspension was measured using a particle size distribution analyzer (Delsa Nano S, from Beckman Coulter, Inc.). As a result, the size distribution had an average particle diameter ($D_v$) of 122 nm, a median particle diameter ($D_{50}$) of 96 nm, and a 90% median diameter ($D_{90}$) of 174 nm.

Comparative Example 19 Experiment of Fine-Pulverizing and Collecting Amphotericin B In a water-cooling type Hoover muller (from Imoto Seisakusho K.K.) were charged and uniformly mixed 0.1 g of the amphotericin B with an average particle diameter of 13,423 nm (melting point: decomposed at 170° C. or higher) used in Example 13 and 1.6 g of fine-pulverized sodium chloride (average particle diameter: 5 μm), and the content was kept in a batter form by slowly adding dropwise 0.36 g of glycerin and fine-pulverized by kneading for 100 cycles at 20° C. Thereafter, the content was placed in 50 mL of a 0.1 mol/L aqueous solution of acetic acid and uniformly dispersed using an ultrasonic apparatus (UT-105, from Sharp Manufacturing System Corporation), but the fine-pulverized particles were floated after centrifugation and could not be recovered. Even when filtration was carried out, the particles could not be recovered because they passed through the filter.

Example 14 Experiment of Fine-Pulverizing Aciclovir

In a water-cooling type Hoover muller (from Imoto Seisakusho K.K.) were charged and uniformly mixed 0.1 g of aciclovir with an average particle diameter of 60,371 nm (melting point: decomposed at about 300° C.) and 1.6 g of fine-pulverized sodium chloride (average particle diameter: 5 μm), and the content was kept in a batter form by slowly adding dropwise 0.1 g of glycerin and fine-pulverized by kneading for 100 cycles at 20° C.

Here, the average aciclovir particle diameter of 60,371 nm before fine-pulverizing is a value measured in the following manner. Five grams of 0.03% sodium lauryl sulfate was first added as a dispersant to 0.01 g of aciclovir and the mixture was uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 60,371 nm, a median particle diameter ($D_{50}$) of 52,997 nm, and a 90% median diameter ($D_{90}$) of 69,371 nm.

In the fine-pulverized and kneaded matter obtained by fine-pulverizing using the water-cooling type Hoover muller (from Imoto Seisakusho K.K.) was uniformly mixed 0.2 g of a purified hydrogenated soybean lecithin-glycerin mixture (weight ratio: 1:3), which was then kneaded in an agate mortar. Thereafter, the content was placed in 50 mL of an aqueous solution and uniformly dispersed using an ultrasonic apparatus (UT-105, from Sharp Manufacturing System Corporation) and then centrifuged (at 6,000 rpm for 10 minutes, using CN-2060 from AS ONE Corporation), followed by removing the supernatant. This operation was carried out three times, and the resultant wet cake was then dried under reduced pressure at 30° C. to provide 0.085 g of a fine-pulverized powder. To 0.01 g of this powder was added 1 mL of a 0.1% aqueous solution of sodium lauryl sulfate, which was then uniformly dispersed using the ultrasonic apparatus (UT-105, from Sharp Manufacturing System Corporation), and 44.99 g of purified water was then added to the dispersion to provide 46.0 g of a suspension. The size distribution of the resultant suspension was measured using a particle size distribution analyzer (Delsa Nano S, from Beckman Coulter, Inc.). As a result, the size distribution had an average particle diameter ($D_v$) of 153 nm, a median particle diameter ($D_{50}$) of 124 nm, and a 90% median diameter ($D_{90}$) of 225 nm.

Comparative Example 20 Experiment of Fine-Pulverizing Aciclovir

In a water-cooling type Hoover muller (from Imoto Seisakusho K.K.) were charged and uniformly mixed 0.1 g of the aciclovir with an average particle diameter of 60,371 nm (melting point: decomposed at about 300° C.) used in Example 14 and 1.6 g of fine-pulverized sodium chloride (average particle diameter: 5 μm), and the content was kept in a batter form by slowly adding dropwise 0.1 g of glycerin and fine-pulverized by kneading for 100 cycles at 20° C. Thereafter, the content was placed in 50 mL of an aqueous solution and uniformly dispersed using an ultrasonic apparatus (UT-105, from Sharp Manufacturing System Corporation), and then centrifuged (at 6,000 rpm for 10 minutes, using CN-2060 from AS ONE Corporation) followed by removing the supernatant. The precipitate was gradually decreased as the operation was repeatedly performed; no precipitate came to be observed when the operation was carried out three times.

Example 15 Experiment of Fine-Pulverizing and Recovering Indomethacin

In a 2-L kneader (from Inoue Mfg., Inc.) were charged and uniformly mixed 38 g of indomethacin with an average particle diameter of 3,960 nm (melting point: 155 to 162° C.) and 608 g of fine-pulverized sodium chloride (average particle diameter: 5 μm), and the content was kept in a batter form by slowly adding dropwise 78 g of glycerin and fine-pulverized at 5° C. for 2 hours. This kneaded matter contains indomethacin having an average particle diameter of 154 nm.

Here, the average particle diameter of indomethacin in the kneaded matter of 154 nm is a value measured in the following manner. Five grams of 0.1% lecithin/0.03% sodium lauryl sulfate was added as a dispersant to 0.05 g of the indomethacin-containing kneaded matter and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 154 nm, a median particle diameter ($D_{50}$) of 118 nm, and a 90% median diameter ($D_{90}$) of 213 nm.

A part (628 g (including 33 g of indomethacin)) of the kneaded matter obtained by fine-pulverizing in the 2-L kneader (from Inoue Mfg., Inc.) and a purified hydrogenated soybean lecithin-glycerin mixture (weight ratio: 1:3) (66 g) were charged and uniformly mixed. Thereafter, a part (about 10 g (including 0.49 g of indomethacin)) of the content was placed in 50 mL of purified water, uniformly dispersed using a homogenizer, and then centrifuged, followed by removing the salt and glycerin. This operation was repeated to wash the supernatant until it reached an electric conductivity of 10 μS/cm or less after centrifugation. The centrifugation washing was performed seven times (8 μS/cm). The resultant wet cake was dried under reduced pressure at 30° C. to provide 0.69 g (including 0.45 g of indomethacin) of a fine-pulverized powder. The recovery rate was 92%. In addition, 5 g of 0.1% sodium lauryl sulfate was added as a dispersant to 0.01 g of the resultant indomethacin-containing fine-pulverized powder and the mixture was uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 137 nm, a median particle diameter ($D_{50}$) of 122 nm, and a 90% median diameter ($D_{90}$) of 164 nm.

Comparative Example 21 Experiment of Fine-Pulverizing and Recovering Indomethacin A part (about 10 g (including 0.51 g of indomethacin)) of the fine-pulverized and kneaded matter obtained in Example 15 was placed in 50 mL of purified water, uniformly dispersed using a homogenizer, and then centrifuged, followed by removing the salt and glycerin. This operation was repeated to wash the supernatant until it reached an electric conductivity of 10 µS/cm or less after centrifugation. The centrifugation washing was performed six times (4 µS/cm). The resultant wet cake was dried under reduced pressure at 30° C. to provide 0.35 g (0.35 g of indomethacin) of a fine-pulverized powder. The recovery rate was 69%. In addition, 5 g of 0.1% sodium lauryl sulfate was added as a dispersant to 0.01 g of the resultant indomethacin-containing fine-pulverized powder and the mixture was uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 1,484 nm, a median particle diameter ($D_{50}$) of 201 nm, and a 90% median diameter ($D_{90}$) of 4,012 nm. Some particles aggregated, which seems to have resulted in larger difference among Dv, $D_{50}$, and $D_{90}$.

Example 16 Experiment of Fine-Pulverizing and Recovering Indomethacin

In a 2-L kneader (from Inoue Mfg., Inc.) were charged and uniformly mixed 38 g of indomethacin with an average particle diameter of 3,960 nm (melting point: 155 to 162° C.), 608 g of fine-pulverized sodium chloride (average particle diameter: 5 µm), and 1.9 g of a carboxyvinyl polymer (Carbopol 980, from Nikko Chemicals Co., Ltd.), and the content was kept in a batter form by slowly adding dropwise 78 g of glycerin and fine-pulverized at 5° C. for 2 hours. This kneaded matter contains indomethacin having an average particle diameter of 96 nm.

Here, the average particle diameter of indomethacin in the kneaded matter of 96 nm is a value measured in the following manner. Five grams of 0.1% lecithin/0.03% sodium lauryl sulfate was added as a dispersant to 0.05 g of the indomethacin-containing kneaded matter and the mixture was uniformly dispersed using an ultrasonic apparatus (UT-105, from Sharp Manufacturing System Corporation), to which 44.95 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 96 nm, a median particle diameter ($D_{50}$) of 72 nm, and a 90% median diameter ($D_{90}$) of 142 nm.

A part (532 g (including 28 g of indomethacin)) of the kneaded matter obtained by fine-pulverizing in the 2-L kneader (from Inoue Mfg., Inc.) and a purified hydrogenated soybean lecithin-glycerin mixture (weight ratio: 1:3) (57 g) were charged and uniformly mixed. Thereafter, a part (about 10 g (including 0.48 g of indomethacin)) of the content was placed in 50 mL of purified water, uniformly dispersed using a homogenizer, and then centrifuged, followed by removing the salt and glycerin. This operation was repeated to wash the supernatant until it reached an electric conductivity of 10 µS/cm or less after centrifugation. The centrifugation washing was performed seven times (4 µS/cm). The resultant wet cake was dried under reduced pressure at 30° C. to provide 0.65 g (including 0.42 g of indomethacin) of a fine-pulverized powder. The recovery rate was 87%. In addition, 5 g of 0.1% sodium lauryl sulfate was added as a dispersant to 0.01 g of the resultant indomethacin-containing fine-pulverized powder and the mixture was uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 94 nm, a median particle diameter ($D_{50}$) of 79 nm, and a 90% median diameter ($D_{90}$) of 125 nm.

Comparative Example 22 Experiment of Fine-Pulverizing and Recovering Indomethacin A part (about 10 g (including 0.54 g of indomethacin)) of the fine-pulverized and kneaded matter of Example 16 was placed in 50 mL of purified water, uniformly dispersed using a homogenizer, and then centrifuged, followed by removing the salt and glycerin. This operation was repeated to wash the supernatant until it reached an electric conductivity of 10 µS/cm or less after centrifugation. The centrifugation washing was performed six times (7 µS/cm). The resultant wet cake was dried under reduced pressure at 30° C. to provide 0.36 g (including 0.36 g of indomethacin) of a fine-pulverized powder. The recovery rate was 67%. In addition, 5 g of 0.1% sodium lauryl sulfate was added as a dispersant to 0.01 g of the resultant indomethacin-containing fine-pulverized powder and the mixture was uniformly dispersed using an ultrasonic apparatus (UT-105, from Sharp Manufacturing System Corporation), to which 44.99 g of purified water was then added to provide 50.0 g of a suspension. The size distribution of the resultant suspension was measured using a particle size distribution analyzer (Delsa Nano S, from Beckman Coulter, Inc.). As a result, the size distribution had an average particle diameter ($D_v$) of 202 nm, a median particle diameter ($D_{50}$) of 163 nm, and a 90% median diameter ($D_{90}$) of 269 nm.

As shown in Examples 13 and 14 and Comparative Examples 19 and 20, the compounds to which the lecithin was added after fine-pulverizing could be recovered as particles, while those to which no lecithin was added could not be so recovered. In the case of Comparative Example 19, this is probably because the particles were present in sufficiently small size and stably and thus were not precipitated by centrifugation and passed through the membrane filter. In the case of Comparative Example 20, it is considered that the particles had larger specific surface area to increase the dissolution rate thereof, and were dissolved during the washing step. In the case of Examples 13 and 14, on the other hand, it is expected that the lecithin exerted actions such as adsorption on the surface of the fine particles, reduced the dissolution rate, and increased the specific gravity, enabling the centrifugation of the particles.

The results of Examples 15 and 16 and Comparative Examples 21 and 22 showed that irrespective of the presence or absence of a carboxyvinyl polymer, the addition of a lecithin improved the recovery rate. The addition of a lecithin also proved to enhance the dispersibility of the particles. These results and the results of Example 12 and Comparative Examples 17 and 18 demonstrate that the mutually contradictory demands of high fine-pulverizing efficiency, high redispersibility, and high collection efficiency could be met.

INDUSTRIAL APPLICABILITY

The method for producing a composite organic compound powder for medical use according to the present invention can be used in the fields of medicines and diagnostic agents because it can convert a poorly water-soluble organic compound into fine grains more safely and simply than before and further can improve the production efficiency (the recovery rate of particles).

The invention claimed is:

1. A method for producing a composite organic compound powder for medical use, comprising:
performing concurrent steps of
mixing a poorly water-soluble and crystalline organic compound powder, a physiologically acceptable salt, a physiologically acceptable polyol and a physiologically acceptable carboxyvinyl polymer which is a water-swellable acrylic acid-based vinyl polymer cross-linked with an allyl ether; and
finely wet-pulverizing the organic compound powder during the mixing by using an amount of the physiologically acceptable carboxyvinyl polymer effective for finely pulverizing the organic compound powder and preventing reaggregation of resulting finely pulverized powder of the poorly water-soluble and crystalline organic compound powder into a powder of larger average diameter; and
removing at least the salt and the polyol from a resulting mixture after the mixing and finely wet-pulverizing steps.

2. The method for producing a composite organic compound powder for medical use according to claim 1, wherein
the poorly water-soluble organic compound powder, the physiologically acceptable salt and the physiologically acceptable carboxyvinyl polymer are mixed together initially,
the physiologically acceptable polyol is added to the initial mixture of the poorly water-soluble organic compound powder, the physiologically acceptable salt and the physiologically acceptable carboxyvinyl polymer, and
the mixing is continued while finely wet-pulverizing the organic compound powder and adding the physiologically acceptable polyol.

3. The method for producing a composite organic compound powder for medical use according to claim 1, further comprising a step of adding a lecithin during or after the finely wet-pulverizing step.

4. The method for producing a composite organic compound powder for medical use according to claim 2, further comprising a step of adding a lecithin during or after the finely wet-pulverizing step.

5. The method for producing a composite organic compound powder for medical use according to claim 1, wherein the resulting mixture after the mixing and finely wet-pulverizing steps is in a batter form containing the finely pulverized organic compound powder and the resulting mixture is maintained in the batter form by adding the physiologically acceptable polyol dropwise.

6. The method for producing a composite organic compound powder for medical use according to claim 1, wherein the organic compound is one or more selected from the group consisting of fenofibrate, felbinac, pranlukast hydrate, miconazole, fluticasone propionate, indomethacin, amphotericin B, aciclovir, nifedipine, nicardipine, nimodipine, dipyridamole, disopyramide, prazosin hydrochloride, prednisolone, cortisone acetate, dexamethasone, betamethasone, beclometasone dipropionate, budesonide, fluocinolone acetonide, naproxen, ketoprofen, 7-(3,5-dimethoxy-4-hydroxycinnamoylamino)-3-octyloxy-4-hydroxy-1-methyl-2 (1H)-quinolinone, phenytoin, phenacemide, ethotoin, primidone, diazepam, nitrazepam, clonazepam, digitoxin, spironolactone, triamterene, chlorthalidone, polythiazide, benzthiazide, griseofulvin, nalidixic acid, chloramphenicol, chlorzoxazine, phenprobamate, mequitazine, bisbentiamine, mitomycin C, bicalutamide, paclitaxel, ubenimex, dacarbazine, fluconazole, rifampicin, triamcinolone acetonide, clemastine fumarate, zafirlukast, dihydrocholesterol, β-carotene, propyl gallate, cinnamic acid, saccharin, folic acid, and maltol.

7. The method for producing a composite organic compound powder for medical use according to claim 1, wherein the physiologically acceptable salt is one or more selected from the group consisting of sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate, and dipotassium hydrogen phosphate.

8. The method for producing a composite organic compound powder for medical use according to claim 1, wherein the polyol is glycerin, propylene glycol or polyethylene glycol.

9. The method for producing a composite organic compound powder for medical use according to claim 1, wherein the physiologically acceptable salt is sodium chloride and the polyol is glycerin.

10. The method for producing a composite organic compound powder for medical use according to claim 1, wherein the amount of the physiologically acceptable carboxyvinyl polymer is 0.002 to 0.9 parts by mass based on 1 part by mass of the organic compound to be finely pulverized.

11. The method for producing a composite organic compound powder for medical use according to claim 1, wherein the initially larger average particle size of the poorly water-soluble and crystalline organic compound powder is from 1088 to 34,000 nm and the resulting average size of the poorly water-soluble and crystalline organic compound powder is from 59 to 338 nm.

12. The method for producing a composite organic compound powder for medical use according to claim 4, wherein the initially larger average particle size of the poorly water-soluble and crystalline organic compound powder is from 1088 to 34,000 nm and the resulting average size of the poorly water-soluble and crystalline organic compound powder is from 96 to 159 nm.

13. The method for producing a composite organic compound powder for medical use according to claim 1, wherein the resulting average size of the poorly water-soluble and crystalline organic compound powder is 400 nm or less.

14. The method for producing a composite organic compound powder for medical use according to claim 4, wherein the resulting average size of the poorly water-soluble and crystalline organic compound powder is 400 nm or less.

15. A method for producing a composite organic compound powder for medical use, comprising:
concurrent steps of
mixing a poorly water-soluble and crystalline organic compound powder, a physiologically acceptable salt, a physiologically acceptable polyol and a physiologically acceptable carboxyvinyl polymer together and forming a mixture of the poorly water-soluble and crystalline organic compound powder, the physiologically acceptable carboxyvinyl polymer containing acrylic acid cross-linked with an ally ether; and finely wet-pulverizing the mixture of the poorly water-soluble and crystalline organic compound powder from an initially larger average particle size to a resulting smaller average particle size; and removing at least the physiologically acceptable salt and the polyol after the concurrent steps of mixing and finely wet-pulverizing, wherein the concurrent steps of mixing and finely wet-pulverizing are carried out using an amount of the physiologically acceptable carboxyvinyl polymer effective for finely pulverizing the organic compound powder and preventing reaggregation of the resulting average particle size of the poorly water-soluble and crystalline organic compound powder into a larger average particle size.

16. The method for producing a composite organic compound powder for medical use according to claim 15, wherein the amount of the physiologically acceptable carboxyvinyl polymer is 0.002 to 0.9 parts by mass based on 1 part by mass of the organic compound to be finely pulverized.

17. The method for producing a composite organic compound powder for medical use according to claim 15, wherein the initially larger average particle size of the poorly water-soluble and crystalline organic compound powder is from 1088 to 34,000 nm and the resulting average size of the poorly water-soluble and crystalline organic compound powder is from 59 to 338 nm.

18. The method for producing a composite organic compound powder for medical use according to claim 15, further comprising a step of adding a lecithin during or after finely wet-pulverizing step, wherein the initially larger average particle size of the poorly water-soluble and crystalline organic compound powder is from 1088 to 34,000 nm and the resulting average size of the poorly water-soluble and crystalline organic compound powder is from 96 to 159 nm.

19. The method for producing a composite organic compound powder for medical use according to claim 15, wherein a resulting average size of the poorly water-soluble and crystalline organic compound powder is 400 nm or less.

20. The method for producing a composite organic compound powder for medical use according to claim 19, wherein the resulting average size of the poorly water-soluble and crystalline organic compound powder is from 20 to 400 nm.

21. The method for producing a composite organic compound powder for medical use according to claim 13, wherein a resulting average size of the poorly water-soluble and crystalline organic compound powder is from 20 to 400 nm.

22. The method for producing a composite organic compound powder for medical use according to claim 14, wherein the resulting average size of the poorly water-soluble and crystalline organic compound powder is from 20 to 400 nm.

* * * * *